United States Patent
Yung et al.

(10) Patent No.: US 11,027,014 B2
(45) Date of Patent: Jun. 8, 2021

(54) METHODS USING GDF-15 ANTIBODIES FOR TREATMENT OF PULMONARY ARTERIAL HYPERTENSION

(71) Applicant: THE BRIGHAM AND WOMEN'S HOSPITAL, INC., Boston, MA (US)

(72) Inventors: Lai-Ming Yung, Jamison, PA (US); Paul B. Yu, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 16/260,914

(22) Filed: Jan. 29, 2019

(65) Prior Publication Data

US 2019/0365857 A1 Dec. 5, 2019

Related U.S. Application Data

(63) Continuation of application No. 15/327,741, filed as application No. PCT/US2015/043373 on Aug. 3, 2015, now abandoned.

(60) Provisional application No. 62/031,924, filed on Aug. 1, 2014.

(51) Int. Cl.

| | |
|---|---|
| *A61K 39/395* | (2006.01) |
| *A61P 11/00* | (2006.01) |
| *C07K 16/22* | (2006.01) |
| *C07K 14/475* | (2006.01) |
| *C07K 14/495* | (2006.01) |
| *A61K 39/00* | (2006.01) |
| *A61K 38/18* | (2006.01) |

(52) U.S. Cl.
CPC .......... *A61K 39/3955* (2013.01); *A61P 11/00* (2018.01); *A61K 38/1841* (2013.01); *A61K 2039/505* (2013.01); *C07K 14/475* (2013.01); *C07K 14/495* (2013.01); *C07K 16/22* (2013.01); *C07K 2317/76* (2013.01); *C07K 2319/30* (2013.01); *C07K 2319/32* (2013.01); *C07K 2319/74* (2013.01)

(58) Field of Classification Search
CPC ...... A61K 39/3955; C07K 16/22; A61P 11/00
See application file for complete search history.

(56) References Cited

U.S. PATENT DOCUMENTS

| | | | |
|---|---|---|---|
| 6,294,350 B1 | 9/2001 | Peterson | |
| 9,809,637 B2 | 11/2017 | Kumar et al. | |
| 2005/0203022 A1 | 9/2005 | Gotwals et al. | |
| 2005/0230022 A1 | 10/2005 | Guerinon et al. | |
| 2007/0014767 A1 | 1/2007 | Ezquerro Saenz et al. | |
| 2007/0077598 A1 | 4/2007 | Breit et al. | |
| 2009/0186016 A1 | 7/2009 | Rade et al. | |
| 2010/0003256 A1 | 1/2010 | Sheppard et al. | |
| 2011/0172296 A1 | 7/2011 | Bennett et al. | |
| 2011/0236309 A1 | 9/2011 | Connor-McCourt et al. | |
| 2011/0319406 A1 | 12/2011 | Kim et al. | |
| 2013/0287688 A1 | 10/2013 | Jain et al. | |
| 2014/0193427 A1* | 7/2014 | Lerner | C07K 16/22 424/158.1 |
| 2015/0056199 A1 | 2/2015 | Kumar et al. | |
| 2015/0239968 A1* | 8/2015 | Wischhusen | C07K 16/22 530/388.24 |
| 2016/0287664 A1 | 10/2016 | Yu et al. | |
| 2017/0137505 A1* | 5/2017 | Gyuris | A61P 9/04 |

FOREIGN PATENT DOCUMENTS

| | | | |
|---|---|---|---|
| CN | 103732623 B | 4/2014 | |
| EP | 0975771 B1 | 7/2007 | |
| KR | 101346132 B1 * | 12/2013 | ............ A61P 35/00 |
| KR | 101346181 B1 * | 1/2014 | ............ A61P 35/00 |
| WO | 1998/048024 A1 | 10/1998 | |
| WO | 1999/065948 A1 | 12/1999 | |
| WO | 2009/026204 A1 | 2/2009 | |
| WO | 2012/093125 A1 | 7/2012 | |
| WO | 2012/145539 A1 | 10/2012 | |
| WO | 2013/019805 A1 | 2/2013 | |
| WO | WO-2013023557 A1 * | 2/2013 | ............ A61P 35/00 |
| WO | 2013/059879 A1 | 5/2013 | |
| WO | WO-2014049087 A1 * | 4/2014 | ............ A61P 35/00 |
| WO | 2015/027082 A1 | 2/2015 | |
| WO | 2015/179227 A1 | 11/2015 | |
| WO | 2015/189790 A1 | 12/2015 | |

OTHER PUBLICATIONS

Wang et al (2013. Cancer Sci. 105(2): 176-185).*
Huang et al, Feb. 2014 (Endocrine-Related Cancer. 21: 39-50).*
Akhurst et al., "Targeting the TGFβ signalling pathway in disease", Nature Reviews Drug Discovery 11(10):790-811 (2012).
Anderton et al., "Induction of heart valve lesions by small-molecule ALK5 inhibitors." Toxicologic Pathology 39(6):916-924 (2011).
Botney et al., "Vascular Remodeling in Primary Pulmonary Hypertension: Potential Role for Transforming Growth Factor-β", American Journal of Pathology 144(2):285-295 (1994).
Chen et al., "Dominant negative mutation of the TGF-β receptor blocks hypoxia-induced pulmonary vascular remodeling", Journal of Applied Physiology 100:564-571 (2006).
Czajkowsky et al., "Fc-fusion proteins: new developments and future perspectives", EMBO Molecular Medicine 4(10):1015-1028 (2012).
Derrett-Smith et al., "Endothelial Injury in a Transforming Growth Factor β-Dependent Mouse Model of Scleroderma Induces Pulmonary Arterial Hypertension", Arthritis & Rheumatism 65(11):2928-2939 (2013).
Gong et al., "Hypoxia induces downregulation of PPAR-γ in isolated pulmonary arterial smooth muscle cells and in rat lung via transforming growth factor-β signaling", American Journal of Physiology—Lung Cellular and Molecular Physiology 301:L899-L907 (2011).

(Continued)

*Primary Examiner* — Zachary C Howard
(74) *Attorney, Agent, or Firm* — Nixon Peabody LLP; David S. Resnick; Ravinderjit S. Braich

(57) ABSTRACT

The technology described herein is directed to methods and compositions for the treatment of hypertension, e.g. pulmonary arterial hypertension, relating to inhibition of TGFβ1, TGFβ3, and/or GDF-15.

3 Claims, 20 Drawing Sheets

Specification includes a Sequence Listing.

(56) References Cited

OTHER PUBLICATIONS

Gonzaelez-Nunez et al., "The ALK-1/SMAD1 pathway in cardiovascular physipathology: a new target for therapy?", Biochem Biophys Acta 1832(10):1492-1510 (2013).
Grafe et al., "Excessive transforming growth factor-β signaling is a common mechanism in osteogenesis imperfecta." Nature Medicine 20(6):670-675 (2014).
Graham et al., "Transforming Growth Factor-β Signaling Promotes Pulmonary Hypertension Caused by Schistosoma Mansoni", Circulation 128:1354-1364 (2013).
Harrison et al., "Transforming Growth Factor-β Receptor Mutations and Pulmonary Arterial Hypertension in Childhood", Circulation 111:435-441 (2005).
Hatton et al., "Transforming growth factor signalling: a common pathway in pulmonary arterial hypertension and systemic sclerosis." International Journal of Clinical Practice 65:35-43 (2011).
Long et al., "Altered Bone Morphogenetic Protein and Transforming Growth Factor-β Signaling in Rat Models of Pulmonary Hypertension: Potential for Activin Receptor-Like Kinase-5 Inhibition in Prevention and Progression of Disease", Circulation 119:566-576 (2009).
Meadows et al., "Increased expressin of growth differentiation factor-15 in systemic sclerosis-associated pulmonary arterial hypetension", Chest 139(5):994-1002 (2010).
Megalou et al., "Transforming growth factor-β inhibition and endothelin receptor blockade in rats with monocrotaline-induced pulmonary hypertension", Pulmonary Circulation 2(4):461-469 (2012).
Megalou et al., "Transforming growth factor-β inhibition attenuates pulmonary arterial hyerptension in rats", International Journal of Clinical and Experimental Medicine 3(4): 332-340 (2010).
Montani et al., "Targeted therapies in pulmonary arterial hypertension", Pharmacology & Therapeutics 141:172-191 (2014).
Nasim et al., "BMPR-II deficiency elicits pro-proliferative and anti-apoptotic response through the activation of TGFβ-TAK1-MAPK pathways in PAH", Human Molecular Genetics 21(11):2548-2558 (2012).
Perkett et al., "Transforming Growth Factor-β Activity in Sheep Lung Lymph during the Development of Pulmonary Hypertension", Journal of Clinical Investigation 86:1459-1464 (1990).
Rabbani et al., "Soluble TGFβ Type II Receptor Gene Therapy Ameliorates Acute Radiation-Induced Pulmonary Injury in Rats", International Journal of Radiation Oncology* Biology* Physics 57(2):563-572 (2003).
Rainer et al., "Cardiomyocyte-Specific Transforming Growth Factor β Suppression Blocks Neutrophil Infiltration, Augments Multiple Cytoprotective Cascades, and Reduces Early Mortality After Myocardial Infarction", Circulation Research 114:1246-1257 (2014).
Samuel et al., "Serelaxin Is a More Efficacious Antifibrotic Than Enalapril in an Experimental Model of Heart Disease", Hypertension 64:315-322 (2014).
Thomas et al., "Activin-like kinase 5 (ALK5) mediates abnormal proliferation of vascular smooth muscle cells from patients with familial pulmonary arterial hypertension and is involved in the progression of experimental pulmonary arterial hypertension induced by monocrotaline." The American Journal of Pathology 174(2):380-389 (2009).
Upton et al., "The transforming growth factor-β-bone morphogenetic protein type signaling pathway in pulmonary vascular homeostasis and disease", Experimental Physiology 98(8):1262-1266 (2013).
Upton et al., "Transforming Growth Factor-β1 Represses Bone Morphogenetic Protein-Mediated Smad Signaling in Pulmonary Artery Smooth Muscle Cells via Smad3", American Journal of Respiratory Cell and Molecular Biology 49(6):1135-1145 (2013).
Yung et al., "A Selective Transforming Growth Factor-β Ligand Trap Attenuates Pulmonary Hypertension", American Journal of Respiratory and Critical Care Medicine 194(9):1140-1151 (2016).
Zaiman et al., "Role of the TGF-β/ALK5 Signaling Pathway in Monocrotaline-induced Pulmonary Hypertension", American Journal of Respiratory and Critical Care Medicine 177:896-905 (2008).
Cao et al., "Changes of calponin and TGFbeta1 in pulmonary artery smooth muscle of pulmonary artery hypertension rats." Chinese Pharmacological Bulletin 23(2):277-278 (2007).
Gordon et al., "Role of transforming growth factor-beta superfamily signaling pathways in human disease", Biochimica et Biophysica Acta, 1782(4): 197-228 (2008).
Ogo et al., "Inhibition of Overactive Transforming Growth Factor-β Signaling by Prostacyclin Analogs in Pulmonary Arterial Hypertension", Am J Respir Cell Mol Biol. 48(6):733-741 (2013).
Li et al. "Purification and Characterization of the Fusion Protein TGF-betaR II/Fc." Chin. J. Cell. Mol. Immunol. 19(4):400-402 (2003) [English Abstract].

* cited by examiner

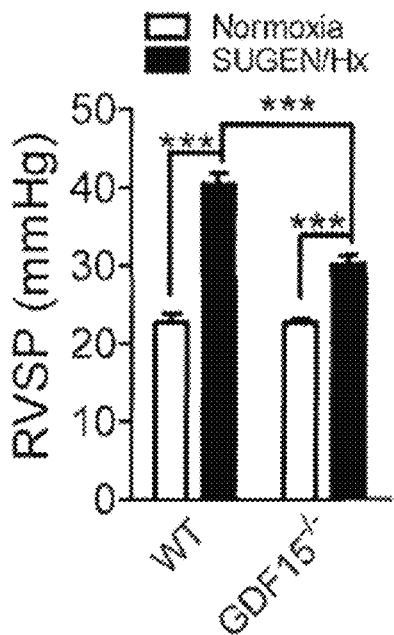
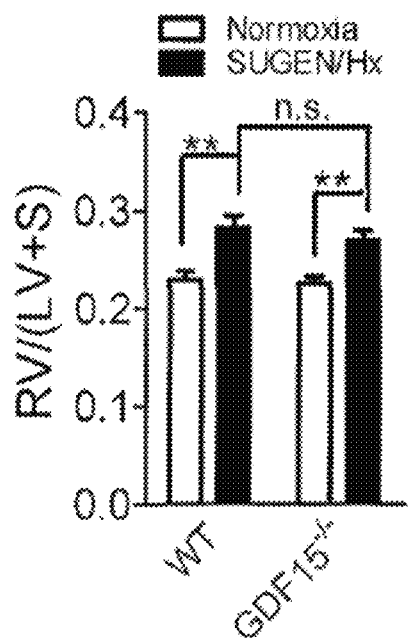
Fig. 6A
Fig. 6B
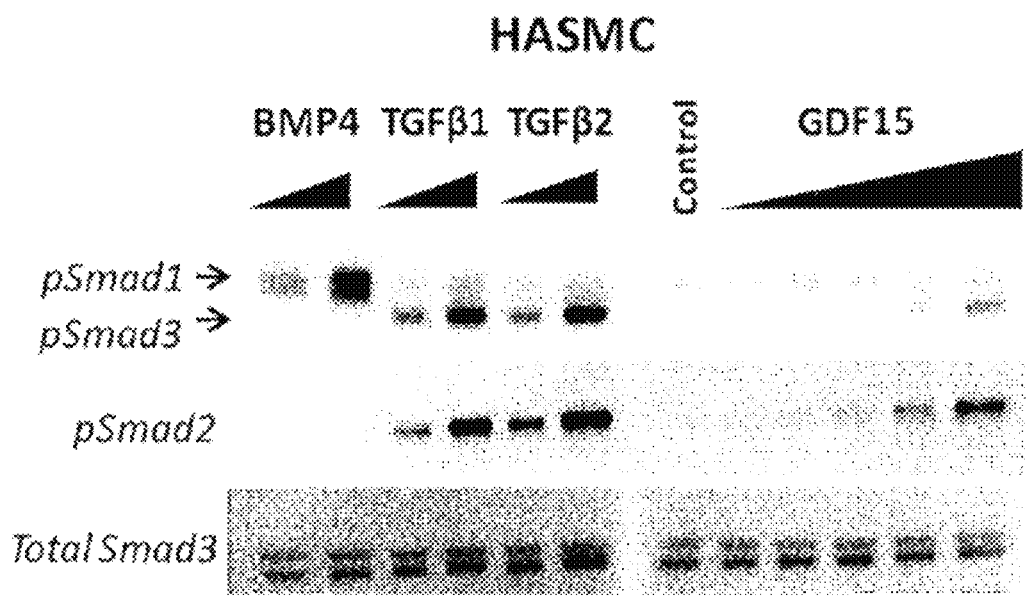
Fig. 7A

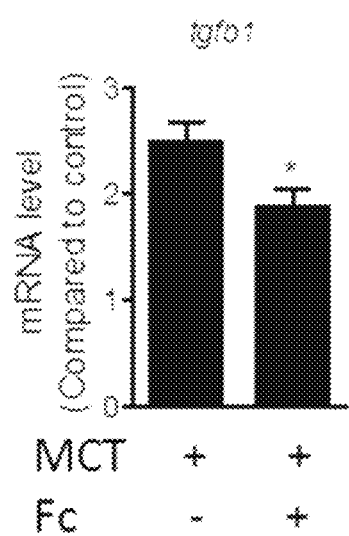 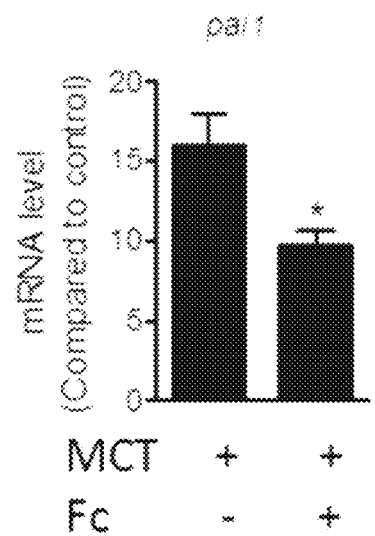 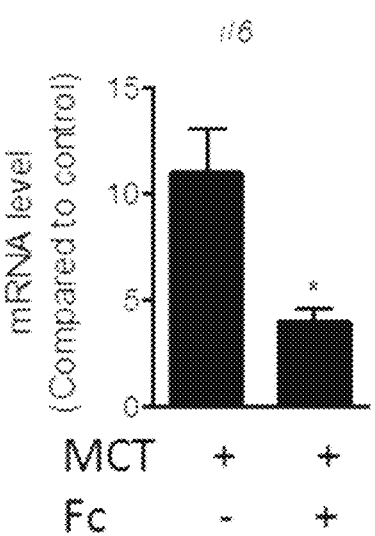
Fig. 15A    Fig. 15B    Fig. 15C
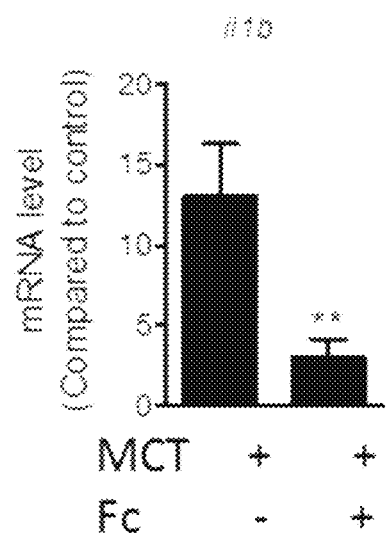 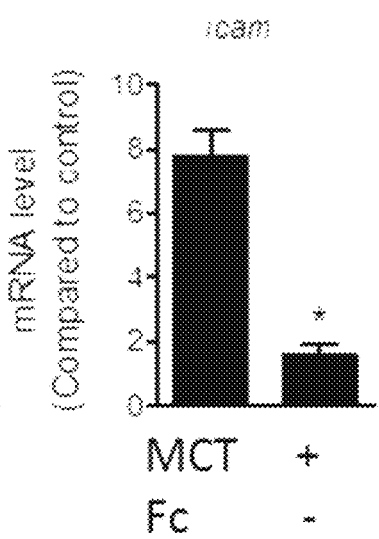
Fig. 15D    Fig. 15E

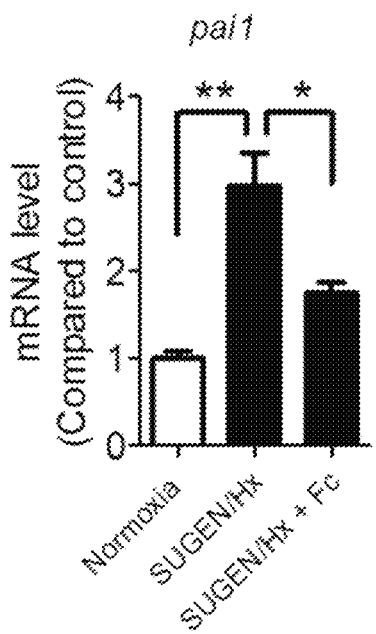
Fig. 16A
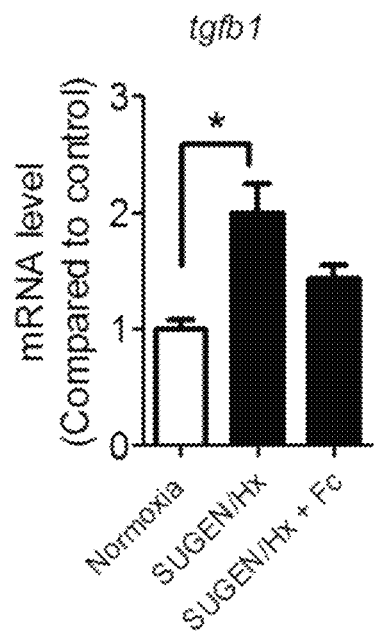
Fig. 16B
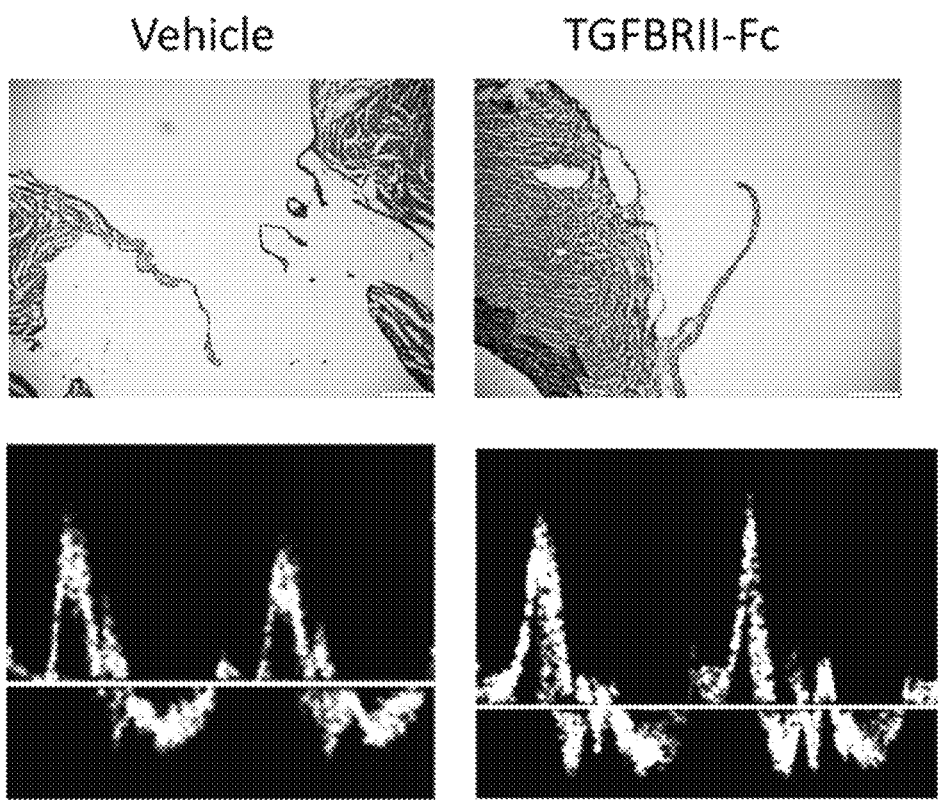
Fig. 17A
Fig. 17B

SEQUENCE LISTING

<160> NUMBER OF SEQ ID NOS: 4

<210> SEQ ID NO 1

```
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 2
<211> LENGTH: 390
<212> TYPE: PRT
<213> ORGANISM: Homo sapiens

<400> SEQUENCE: 2

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30
```

Cys Lys Thr Ile Asp Met Glu Leu Val Lys Arg Lys Arg Ile Glu Ala
                35                  40                  45

Ile Arg Gly Gln Ile Leu Ser Lys Leu Arg Leu Ala Ser Pro Pro Ser
 50                  55                  60

Gln Gly Glu Val Pro Pro Gly Pro Leu Pro Glu Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
                115                 120                 125

His Ser Ile Tyr Met Phe Phe Asn Thr Ser Glu Leu Arg Glu Ala Val
            130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
                195                 200                 205

Ser Arg Gly Gly Glu Ile Glu Gly Phe Arg Leu Ser Ala His Cys Ser
            210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385                 390

<210> SEQ ID NO 3
<211> LENGTH: 412
<212> TYPE: PRT
<213> ORGANISM: Homo sapiens

<400> SEQUENCE: 3

Met Lys Met His Leu Gln Arg Ala Leu Val Val Leu Ala Leu Leu Asn

```
  1               5                  10                 15
    Phe Ala Thr Val Ser Leu Ser Leu Ser Thr Cys Thr Thr Leu Asp Phe
                 20                 25                 30

Gly His Ile Lys Lys Arg Val Glu Ala Ile Arg Gly Gln Ile Leu
                 35                 40                 45

Ser Lys Leu Arg Leu Thr Ser Pro Glu Pro Thr Val Met Thr His
    50                  55                 60

Val Pro Tyr Gln Val Leu Ala Leu Tyr Asn Ser Thr Arg Glu Leu Leu
    65                  70                 75                 80

Glu Glu Met His Gly Glu Arg Glu Gly Cys Thr Gln Glu Asn Thr
                 85                 90                 95

Glu Ser Glu Tyr Tyr Ala Lys Glu Ile His Lys Phe Asp Met Ile Gln
                 100                105                110

Gly Leu Ala Glu His Asn Glu Leu Ala Val Cys Pro Lys Gly Ile Thr
                 115                120                125

Ser Lys Val Phe Arg Phe Asn Val Ser Ser Val Glu Lys Asn Arg Thr
    130                 135                140

Asn Leu Phe Arg Ala Glu Phe Arg Val Leu Arg Val Pro Asn Pro Ser
    145                 150                155                160

Ser Lys Arg Asn Glu Gln Arg Ile Glu Leu Phe Gln Ile Leu Arg Pro
                 165                170                175

Asp Glu His Ile Ala Lys Gln Arg Tyr Ile Gly Gly Lys Asn Leu Pro
                 180                185                190

Thr Arg Gly Thr Ala Glu Trp Leu Ser Phe Asp Val Thr Asp Thr Val
                 195                200                205

Arg Glu Trp Leu Leu Arg Arg Glu Ser Asn Leu Gly Leu Glu Ile Ser
    210                 215                220

Ile His Cys Pro Cys His Thr Phe Gln Pro Asn Gly Asp Ile Leu Glu
    225                 230                235                240

Asn Ile His Glu Val Met Glu Ile Lys Phe Lys Gly Val Asp Asn Glu
                 245                250                255

Asp Asp His Gly Arg Gly Asp Leu Gly Arg Leu Lys Lys Gln Lys Asp
                 260                265                270

His His Asn Pro His Leu Ile Leu Met Met Ile Pro Pro His Arg Leu
                 275                280                285

Asp Asn Pro Gly Gln Gly Gln Arg Lys Arg Ala Leu Asp Thr
    290                 295                300

Asn Tyr Cys Phe Arg Asn Leu Glu Glu Asn Cys Cys Val Arg Pro Leu
    305                 310                315                320

Tyr Ile Asp Phe Arg Gln Asp Leu Gly Trp Lys Trp Val His Glu Pro
                 325                330                335

Lys Gly Tyr Tyr Ala Asn Phe Cys Ser Gly Pro Cys Pro Tyr Leu Arg
                 340                345                350

Ser Ala Asp Thr Thr His Ser Thr Val Leu Gly Leu Tyr Asn Thr Leu
                 355                360                365

Asn Pro Glu Ala Ser Ala Ser Pro Cys Cys Val Pro Gln Asp Leu Glu
    370                 375                380

Pro Leu Thr Ile Leu Tyr Tyr Val Gly Arg Thr Pro Lys Val Glu Gln
    385                 390                395                400

Leu Ser Asn Met Val Val Lys Ser Cys Lys Cys Ser
                 405                410

<210> SEQ ID NO 4
```

```
<211> LENGTH: 592
<212> TYPE: PRT
<213> ORGANISM: Homo sapiens

<400> SEQUENCE: 4

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
```

-continued

```
              385                 390                 395                 400

Val His Arg Asp Leu Lys Ser Ser Asn Ile Leu Val Lys Asn Asp Leu
                         405                 410                 415

Thr Cys Cys Leu Cys Asp Phe Gly Leu Ser Leu Arg Leu Asp Pro Thr
                         420                 425                 430

Leu Ser Val Asp Asp Leu Ala Asn Ser Gly Gln Val Gly Thr Ala Arg
                         435                 440                 445

Tyr Met Ala Pro Glu Val Leu Glu Ser Arg Met Asn Leu Glu Asn Val
                 450                 455                 460

Glu Ser Phe Lys Gln Thr Asp Val Tyr Ser Met Ala Leu Val Leu Trp
         465                 470                 475                 480

Glu Met Thr Ser Arg Cys Asn Ala Val Gly Glu Val Lys Asp Tyr Glu
                         485                 490                 495

Pro Pro Phe Gly Ser Lys Val Arg Glu His Pro Cys Val Glu Ser Met
                         500                 505                 510

Lys Asp Asn Val Leu Arg Asp Arg Gly Arg Pro Glu Ile Pro Ser Phe
                         515                 520                 525

Trp Leu Asn His Gln Gly Ile Gln Met Val Cys Glu Thr Leu Thr Glu
                 530                 535                 540

Cys Trp Asp His Asp Pro Glu Ala Arg Leu Thr Ala Gln Cys Val Ala
         545                 550                 555                 560

Glu Arg Phe Ser Glu Leu Glu His Leu Asp Arg Leu Ser Gly Arg Ser
                         565                 570                 575

Cys Ser Glu Glu Lys Ile Pro Glu Asp Gly Ser Leu Asn Thr Thr Lys
                         580                 585                 590
```

METHODS USING GDF-15 ANTIBODIES FOR TREATMENT OF PULMONARY ARTERIAL HYPERTENSION

CROSS-REFERENCE TO RELATED APPLICATIONS

This application is a continuation under 35 U.S.C. § 120 of co-pending U.S. application Ser. No. 15/327,741 filed Jan. 20, 2017, which is a 35 U.S.C. § 371 National Phase Entry Application of International Application No. PCT/US2015/043373 filed Aug. 3, 2015, which designates the U.S. and claims benefit under 35 U.S.C. § 119(e) of U.S. Provisional Application No. 62/031,924 filed Aug. 1, 2014, the contents of which are incorporated herein by reference in their entireties.

GOVERNMENT SUPPORT

This invention was made with government support under Grant No. 5 K08 HL079943 05 awarded by the National Institutes of Health. The U.S. government has certain rights in the invention.

SEQUENCE LISTING

The sequence listing of the present application has been submitted electronically via EFS-Web as an ASCII formatted sequence listing with a file name "043214-082451-PCT_SL", creation date of Aug. 19, 2015 and a size of 15,083 bytes. The sequence listing submitted via EFS-Web is part of the specification and is herein incorporated by reference in its entirety.

TECHNICAL FIELD

The technology described herein relates to the treatment of fibrosis and/or hypertension, e.g. pulmonary arterial hypertension.

BACKGROUND

TGF-β signaling inhibition has been attempted in order to treat pulmonary arterial hyperstion, but existing strategies (e.g., inhibition of the Activin/TGF-β type I kinase receptors ALK4/ALK5/ALK7 or non-selective neutralization of all TGFβ ligands) induce serious side effects such as hemorrhagic valve necrosis, or abnormalities of bone mineralization and maturation, or significant side effects such as skin rashes and lesions, epistaxis, or gingival bleeding. A more specific approach to modulation of this signaling cascade could permit effective and safe treatment of hypertension.

SUMMARY

As described herein, the inventors have found that inhibition of TGFβ signaling by focused inhibition of the ligand TGF-β1; TGF-β3 and/or GDF15 can treat pulmonary arterial hypertension without inducing the side effects caused by broad inhibition of Activin/TGFβ ligands signaling receptor-ligand interactions.

In one aspect, described herein is a method of treating hypertension or fibrosis in a subject in need of treatment thereof, the method comprising administering an inhibitor of GDF-15; TGβ1; and/or TGFβ3 to the subject. In some embodiments, the hypertension is pulmonary arterial hypertension (PAH). In some embodiments, the subject is a subject having or diagnosed as having pulmonary arterial hypertension (PAH). In some embodiments, the fibrosis is fibrosis associated with a disease or condition selected from the group consisting of: emphysema; COPD; interstitial lung disease and pulmonary fibrosis; idiopathic pulmonary fibrosis; scleroderma lung disease; interstitial or pulmonary vascular disease; bleomycin induced lung injury; pulmonary fibrosis due to exposure to chemotherapeutic drugs (methotrexate, cyclophosphamide) or other toxins; chronic lung disease associated with prematurity, a.k.a., bronchopulmonary dysplasia; pulmonary fibrosis or interstitial lung disease associated with exposure to antiarrhythmic drugs (e.g. amiodarone); and interstitial lung disease associated with exposure to asbestos, silica, or grain. In some embodiments, the subject is a subject having or diagnosed as having a disease or condition selected from the group consisting of: emphysema; COPD; interstitial lung disease and pulmonary fibrosis; idiopathic pulmonary fibrosis; scleroderma lung disease; interstitial or pulmonary vascular disease; bleomycin induced lung injury; pulmonary fibrosis due to exposure to chemotherapeutic drugs (methotrexate, cyclophosphamide) or other toxins; chronic lung disease associated with prematurity, a.k.a., bronchopulmonary dysplasia; pulmonary fibrosis or interstitial lung disease associated with exposure to antiarrhythmic drugs (e.g. amiodarone); and interstitial lung disease associated with exposure to asbestos, silica, or grain.

In some embodiments, the inhibitor inhibits TGFβ1. In some embodiments, the inhibitor inhibits TGFβ3. In some embodiments, the inhibitor inhibits TGFβ1 and TGFβ3. In some embodiments, the inhibitor inhibits GDF15. In some embodiments, the inhibitor further inhibits TGFβ1 and/or TGFβ3. In some embodiments, the inhibitor is specific for GDF15. In some embodiments, the inhibitor is specific for TGFβ1. In some embodiments, the inhibitor is specific for TGFβ3.

In some embodiments, the inhibitor is an antibody reagent or ligand trap. In some embodiments, the ligand trap is a TGFβ-1/3 GDF-15 ligand trap. In some embodiments, the ligand trap is TGFBRII-Fc.

In some embodiments, the subject has scleroderma or connective tissue disease associated with PAH (APAH-CTD). In some embodiments, the subject is determined to have an increased level of GDF-15, TGFβ1, and/or TGFβ3 relative to a control. In some embodiments, the subject is determined to have an increased level of GDF-15, TGFβ1, and/or TGFβ3 relative to the average level of GDF-15, TGFβ1, and/or TGFβ3 in subjects having PAH but not showing symptoms of scleroderma or APAH-CTD.

BRIEF DESCRIPTION OF THE DRAWINGS

FIGS. 6A-6B demonstrate that transgenic mice can be used to ascertain the pathogenetic role of GDF15. GDF15 knockout mice are protected against SUGEN/Hypoxia-induced PAH.  $p<0.01$ and* $p<0.001$ as shown.

FIGS. 7A-7B demonstrate that consistent with the data in pulmonary vascular smooth muscle cells, GDF15 induced potent TGFb signaling in human aortic smooth muscle cells (HASMC) in vitro. BMP4, TGFb1 and TGFb2 were used as positive controls.

FIGS. 15A-15E demonstrate that treatment with TGFBRII-Fc following establishment of PAH is associated with partial rescue of PAH and mortality. Following MCT treatment, rats were administered TGFBRII-Fc (15 mg/kg three time weekly) in a delayed fashion starting on day 17, after the establishment of PAH. Delayed treatment with TGFBRII-Fc reduced the expression of TGFβ1, PAI-1, IL-6, IL1b, and ICAM-1 in the lung tissues of MCT-treated rats, n=3-5 (FIG. 15A-15E).

FIGS. 16A-16B demonstrate the efficacy of TGFBRII-Fc in a murine model of PAH. Adult male mice were treated with SUGEN and exposed to hypoxia for 3 weeks. TGFBRII-Fc treatment prevented the up-regulation of PAI-1 (FIG. 16A) and trended towards reduced TGFβ1 (FIG. 16B) mRNA levels in lungs of SUGEN-hypoxia treated mice (n=6-8). Scale bar=50 μm.

FIGS. 17A-17B demonstrate that chronic treatment with TGFBRII-Fc was not associated with morphological changes in mitral valve structure, with no evidence of sclerotic or degenerative remodeling. Histology of mitral valves in vehicle and TGFBRII-Fc treated rats, scale bar=500 μm (FIG. 17A). Representative tracing from echocardiogram showing normal mitral regurgitation in vehicle- and TGFBRII-Fc treated rats (FIG. 17B).

DETAILED DESCRIPTION

Figure 1A:
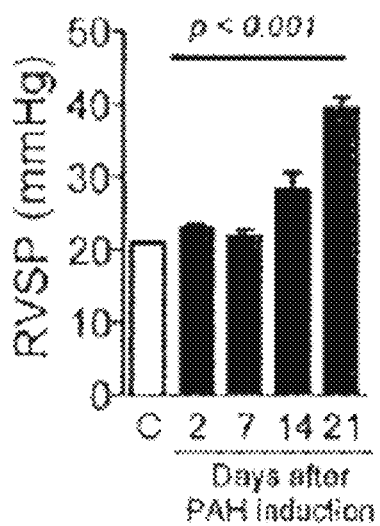
FIGS. 1A-1H demonstrate that monocrotaline (MCT) induced pulmonary hypertension in rats is associated with increased PAI-1 transcriptional activity and elevated GDF15 mRNA level. Changes in right ventricular systolic pressure (RVSP, FIG. 1A) and right ventricular hypertrophy (RVH, FIG. 1B) were measured at various intervals after treatment of Sprague Dawley rats with MCT (40 mg/kg SC). RVSP was measured by right ventricular catheterization, and RVH was determined by the ratio of the weight of the right ventricular (RV) free wall to the sum of the left ventricular and septal (LV+S) walls (n=3 per time point). Quantitative RT-PCR of lungs of MGT-treated rats revealed increased TGF-β signaling, reflected by the elevated PAI-1 (FIG. 1C) and TGFb1 transcription activity (FIG. 1D). Impaired BMP signaling activity as shown by decreased ld1 (FIG. 1E) and BMPR2 (FIG. 1F) mRNA levels. Expression of TGFb3 remained unaffected in lungs of MGT-treated rats (FIG. 1G). Elevated levels of GDF15 were also found in lungs of MGT-treated rats. * $p<0.05$ and ** $p<0.01$ compared to control rats (FIG. 1H).

As described herein, the inventors have discovered that inhibition of TGFβ1, TGFβ3, and/or GDF15 via a recombinant ligand trap, TGFBRII-Fc, reduces TGF-β signaling and improves pulmonary arterial hypertension (PAH). This approach of targeting the receptor's ligand suffers from fewer side effects and toxicity than targeting all Activin and TGF-β receptors (i.e., ALK4, ALK5 and ALK7) and/or all of the receptor's ligands.

In one aspect, described herein is a method of treating hypertension or fibrosis in a subject in need of treatment thereof, the method comprising administering an inhibitor of GDF-15; TGFβ1; and/or TGFβ3 to the subject.

As used herein, "hypertension," also referred to as "HTN" or "high blood pressure" or "arterial hypertension," refers to a medical condition in which the blood pressure in the arteries is elevated. This requires the heart to work harder than normal to circulate blood through the blood vessels. Blood pressure is summarised by two measurements, systolic and diastolic, which depend on whether the heart muscle is contracting (systole) or relaxed between beats (diastole) and equate to a maximum and minimum pressure, respectively. Normal blood pressure at rest is within the range of 100-140 mmHg systolic (top reading) and 60-90 mmHg diastolic (bottom reading). High blood pressure is said to be present if it is persistently at or above 140/90 mmHg. Hypertension is a major risk factor for stroke, myocardial infarction (heart attacks), heart failure or chronic heart failure (CHF), aneurysms of the arteries (e.g. aortic aneurysm), peripheral arterial disease and is a cause of chronic kidney disease. Even moderate elevation of arterial blood pressure is associated with a shortened life expectancy. Dietary and lifestyle changes can improve blood pressure control and decrease the risk of associated health complications, although drug treatment is often necessary in people for whom lifestyle changes prove ineffective or insufficient. In some embodiments, the hypertension is pulmonary arterial hypertension (PAH). In some embodiments, is a subject having or diagnosed as having pulmonary arterial hypertension (PAH). In one aspect, described herein is a method of treating pulmonary arterial hypertension (PAH) in a subject in need of treatment thereof, the method comprising administering an inhibitor of TGFβ1, TGFβ3 and/or GDF15 to the subject. As used herein, "pulmonary arterial hypertension" or "PAH" refers to a type of pulmonary hypertension (e.g. high blood pressure in the vasculature of the lungs) in which the pulmonary arteries constrict abnormally.

As used herein, "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. Fibrosis can occur as the result of inflammation, irritation, or healing. In some embodiments, the fibrosis is fibrosis associated with a disease or condition selected from the group consisting of emphysema; COPD; interstitial lung disease and pulmonary fibrosis; idiopathic pulmonary fibrosis; scleroderma lung disease; interstitial or pulmonary vascular disease; bleomycin induced lung injury; pulmonary fibrosis due to exposure to chemotherapeutic drugs (methotrexate, cyclophosphamide) or other toxins; chronic lung disease associated with prematurity, a.k.a., bronchopulmonary dysplasia; pulmonary fibrosis or interstitial lung disease associated with exposure to antiarrhythmic drugs (e.g. amiodarone); and interstitial lung disease associated with exposure to asbestos, silica, or grain. In some embodiments, the subject is a subject having or diagnosed as having a disease or condition selected from the group consisting of: emphysema; COPD; interstitial lung disease and pulmonary fibrosis; idiopathic pulmonary fibrosis; scleroderma lung disease; interstitial or pulmonary vascular disease; bleomycin induced lung injury; pulmonary fibrosis due to exposure to chemotherapeutic drugs (methotrexate, cyclophosphamide) or other toxins; chronic lung disease associated with prematurity, a.k.a., bronchopulmonary dysplasia; pulmonary fibrosis or interstitial lung disease associated with exposure to antiarrhythmic drugs (e.g. amiodarone); and interstitial lung disease associated with exposure to asbestos, silica, or grain.

The methods and compositions described herein relate to inhibitors of TGFβ1, TGFβ3, and/or GDF15. As used herein, "GDF-15" refers to Growth and Differentiation Factor 15 (NCBI Gene ID No: 9518), a member of the Transforming Growth Factor-beta superfamily of growth factors. GDF15 is known to bind TGFβ superfamily type I receptors including TGFBRII. The sequence of GDF-15 is known in the art for a number of species, e.g., human GDF-15 (polypeptide sequence: SEQ ID NO: 1, NCBI Ref Seq: NP_004855).

As used herein, "TGFβ1" refers to Transforming Growth Factor Beta 1 (NCBI Gene ID No: 7040), a member of the Transforming Growth Factor-beta superfamily of growth factors. TGFβ1 is known to bind TGFβ superfamily type I receptors including TGFBRII. The sequence of TGFβ1 is known in the art for a number of species, e.g., human TGFβ1 (polypeptide sequence: SEQ ID NO: 2, NCBI Ref Seq: NP_000651).

As used herein, "TGFβ3" refers to Transforming Growth Factor Beta 3 (NCBI Gene ID No: 7043), a member of the Transforming Growth Factor-beta superfamily of growth factors. TGFβ3 is known to bind TGFβ superfamily type I receptors including TGFBRII. The sequence of TGFβ3 is known in the art for a number of species, e.g., human TGFβ3 (polypeptide sequence: SEQ ID NO: 3, NCBI Ref Seq: NP_003032).

As used herein, "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, TGFβ1, TGFβ3, and/or GDF15, e.g. its ability to decrease the level and/or activity of TGFβ1, TGFβ3, and/or GDF15 can be determined, e.g. by measuring the level of an expression product of TGFβ1, TGFβ3, and/or GDF15 and/or the activity of TGFβ1, TGFβ3, and/or GDF15. Methods for measuring the level of a given mRNA and/or polypeptide are known to one of skill in the art, e.g. quantitative RT-PCR with primers can be used to determine the level of RNA and Western blotting with an antibody (e.g. an anti-TGFβ1 and/or TGFβ3 antibody, e.g. Monclonal antibody 1D11) can be used to determine the level of a polypeptide. The activities of TGFβ1, TGFβ3, and/or GDF15 can be determined using methods known in the art and described elsewhere herein, e.g., by measuring the level of TGFβ1, TGFβ3, and/or GDF15 bound to TGFBRII, or detecting the level of, e.g., PAI1 mRNA, wherein decreased levels of those mRNAs indicate decreased levels of TGFβ1, TGFβ3, and/or GDF15 activity. In some embodiments, the inhibitor can be an inhibitory nucleic acid; an aptamer; an antibody reagent; an antibody; or a small molecule.

In some embodiments, the inhibitor can be an antibody reagent. In some embodiments, the inhibitor can be a ligand trap. As described herein, "ligand trap" refers to an engineered polypeptide which comprises at least a portion of a protein that binds the target molecule (e.g. TGFβ1, TGFβ3, and/or GDF15). The portion of the protein that binds the target molecule can be, e.g. the extracellular domain of a receptor, a soluble version of a receptor, the binding domain of a receptor, and the like. In some embodiments, the ligand trap can further comprise a second domain that comprises an Ig constant domain, e.g., an IgG constant domain (e.g. IgG1) and/or a human Ig constant domain. The second domain can, e.g., improve the half-life of the ligand trap. In some embodiments, the ligand trap can be a TGFβ1, TGFβ3, and/or GDF15 ligand trap. In some embodiments, the ligand trap can be a GDF-15 and TGFβ1 and/or TGFβ3 ligand trap. In some embodiments, the ligand trap can be a TGFβ-1/3 GDF-15 ligand trap, e.g., it can bind to all three ligands. In some embodiments, the ligand trap can be TGFBRII-Fc. As used herein, "TGFBRII-Fc" refers to a ligand trap comprising the extracellular domain of TGFBRII and/or a soluble decoy receptor for TGFBRII. In some embodiments, TGFBRII-Fc can be purchased commercially (e.g. Cat No. 341-BR, 1003-RT, 1600-R2 or 532-R2; R&D Systems; Minneapolis, Minn.). TGFBRII-Fc can also be obtained from Acceleron (Cambridge, Mass.). In some embodiments, the TGFBRII-Fc can comprise amino acids 23-159, 23-184, 24-159, 24-184, 23-176, 24-176, 73-159, 73-184, 73-176 of SEQ ID NO: 4.

In some embodiments, the inhibitor is specific for GDF-15. In some embodiments, the inhibitor is semi-selective, e.g., it has inhibitory effects against additional TGFBR1 ligands, but not all TGFβ ligands. In some embodiments, the inhibitor can inhibit, in addition to GDF-15, TGFβ1 (e.g., NCBI Gene ID: 7040) and/or TGFβ3 (e.g., NCBI Gene ID: 7043).

It is demonstrated herein that antagonism of GDF-15 using TGFBRII-Fc, a TGF-beta1/3, GDF-15 ligand trap, improves pulmonary arterial hypertension (PAH) in two animal models. Knockout mice lacking GDF-15 are relatively protected against the development of pulmonary arterial hypertension. Previous approaches to inhibiting TGF-beta signaling as therapy in PAH used strategies which inhibited all TGF-beta ligands, by inhibiting the TGFbeta type I receptor kinase ALK5, or neutralizing all TGF-beta ligands using a pan-TGF-beta antibody. Although effective in animal models, these strategies have been limited by various toxicities, including hemorrhagic valve necrosis, and abnormalities of bone mineralization and maturation due to the constitutive function of several of these TGF-beta ligands.

As described herein, semi-selective inhibition of TGF-beta ligands 1 and 3 using TGFBRII-Fc is still effective, and well tolerated. TGFβ1, TGFβ3, and/or GDF15 are identified herein as being a potentially important targets of this therapy. Further, they have shown that genetic ablation of GDF-15 attenuates PAH significantly, and that an effective neutralizing antibody against GDF-15 attenuates PAH.

A humanized, or human-derived monoclonal antibody specific for GDF-15 is administratable periodically to patients with various types of pulmonary arterial hypertension. Certain patients with specific etiologies of PAH, i.e., scleroderma, or connective tissue disease associated PAH (APAH-CTD), who are known to have particularly higher levels of GDF-15 benefit more from treatment with a neutralizing antibody.

In various embodiments, the present invention provides antibodies, peptides, and nucleic acids, and methods of using the same, that inhibit GDF-15 when administered to a patient. Such GDF-15 inhibition may be carried out in the patient for the purpose of treating a condition in the patient. The condition may be, but is not limited to being, pulmonary arterial hypertension.

In some embodiments, the methods described herein relate to treating a subject having or diagnosed as having hypertension (e.g., PAH) with an inhibitor of GDF-15. Subjects having hypertension can be identified by a physician using current methods of diagnosing hypertension. Symptoms and/or complications of hypertension which characterize these conditions and aid in diagnosis are well known in the art and include but are not limited to, headaches, vertigo, tinnitus, dizziness, or fainting. Tests that may aid in a diagnosis of, e.g. hypertension include, but are not limited to, blood pressure measurements. A family history of hypertension can also aid in determining if a subject is likely to have hypertension or in making a diagnosis of hypertension.

In some embodiments, the subject treated according the methods described herein can be a subject having and/or diagnosed as having scleroderma or connective tissue disease associated with PAH (APAH-CTD).

In some embodiments, the subject treated according the methods described herein can be a subject having and/or determined to have an increased level of GDF-15, TGFβ1, and/or TGFβ3 relative to a control. In some embodiments, the increased level of GDF-15, TGFβ1, and/or TGFβ3 can be an increased level of circulating GDF-15, TGFβ1, and/or TGFβ3. In some embodiments, the control can be the level of GDF-15, TGFβ1, and/or TGFβ3a healthy subject and/or population of healthy subject. In some embodiments, the control can be the level of GDF-15, TGFβ1, and/or TGFβ3 in a subject and/or population of subjects having PAH but not showing symptoms of scleroderma or APAH-CTD.

The compositions and methods described herein can be administered to a subject having or diagnosed as having hypertension, e.g., PAH. In some embodiments, the methods described herein comprise administering an effective amount of compositions described herein, e.g. an inhibitor of GDF-15 to a subject in order to alleviate a symptom of hypertension, e.g. PAH. As used herein, "alleviating a symptom of hypertension" is ameliorating any condition or symptom associated with the hypertension. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of an inhibitor of GDF-15 needed to alleviate at least one or more symptom of the disease or disorder, and relates to a sufficient amount of pharmacological composition to provide the desired effect. The term "therapeutically effective amount" therefore refers to an amount of an inhibitor of GDF-15 that is sufficient to provide a particular anti-hypertensive effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the inhibitor of GDF-15, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for blood pressure, among others. The dosage can be determined by a physician and adjusted, as necessary, to suit observed effects of the treatment.

In some embodiments, the technology described herein relates to a pharmaceutical composition comprising an inhibitor of GDF-15 as described herein, and optionally a pharmaceutically acceptable carrier. In some embodiments, the active ingredients of the pharmaceutical composition comprise an inhibitor of GDF-15 as described herein. In some embodiments, the active ingredients of the pharmaceutical composition consist essentially of an inhibitor of GDF-15 as described herein. In some embodiments, the active ingredients of the pharmaceutical composition consist of an inhibitor of GDF-15 as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an inhibitor of GDF-15 as described herein.

In some embodiments, the pharmaceutical composition comprising an inhibitor of GDF-15 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an inhibitor of GDF-15 as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of the inhibitor as disclosed herein can also be incorporated into the parenteral dosage forms of the disclosure, including conventional and controlled-release parenteral dosage forms.

Pharmaceutical compositions comprising an inhibitor of GDF-15 can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the inhibitor of GDF-15 can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include calcium channel blockers (e.g. verapamil, diltiazem, and dihydropyridines), angiotensin converting enzyme inhibitors (ACE-I)(e.g., captopril, enalapril, fosinopril, lisinopril, perindopril, quinapril, ramipril, trandolapril, and benazepril), ARBs (candesartan, eprosartan, irbesartan, losartan, olmesartan, telmisartan, and valsartan), thiazide diuretics, beta-blockers (e.g., atenolol, metoprolol, nadolol, nebivolol, oxprenolol, pindolol, propranolol, and timolol), and alpha-blockers (e.g., doxazosin, phentolamine, indoramin, phenoxybenzamine, prazosin, terazosin, and tolazoline).

In certain embodiments, an effective dose of a composition comprising an inhibitor of GDF-15 as described herein can be administered to a patient once. In certain embodiments, an effective dose of a composition comprising an inhibitor of GDF-15 can be administered to a patient repeatedly. For systemic administration, subjects can be administered a therapeutic amount of a composition comprising an inhibitor of GDF-15 such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. blood pressure by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an inhibitor of GDF-15 can be administered over a period of time, such as over a 5 minute, 10 minute, 15 minute, 20 minute, or 25 minute period.

The dosage ranges for the administration of an inhibitor of GDF-15, according to the methods described herein depend upon, for example, the form of the inhibitor, its potency, and the extent to which symptoms, markers, or indicators of a condition described herein are desired to be reduced, for example the percentage reduction desired for blood pressure. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an inhibitor of GDF-15 in, e.g. the treatment of a condition described herein, or to induce a response as described herein (e.g. a decrease in blood pressure) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. blood pressure. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. blood pressure). It is well within the ability of one skilled in the art to monitor efficacy of administration and/or treatment by measuring any one of such parameters, or any combination of parameters. Efficacy can be assessed in animal models of a condition described herein, for example treatment of a mouse model of PAH. When using an experimental animal model, efficacy of treatment is evidenced when a statistically significant change in a marker is observed, e.g. blood pressure.

In vitro and animal model assays are provided herein which allow the assessment of a given dose of an inhibitor of GDF-15. By way of non-limiting example, the effects of a dose of an inhibitor of GDF-15 can be assessed by contacting a cell with the inhibitor and measuring the expression of, e.g. PAI1 and/or IL6, where a decrease in those levels indicates inhibition of GDF-15.

The efficacy of a given dosage combination can also be assessed in an animal model, e.g. a mouse model of hypertension. For example, mice can be treated with monocrotaline (MCT) to induce pulmonary hypertension and then treated with an inhibitor of GDF-15. Right ventricular systolic pressure (RVSP) can be measured by right ventricular catheterization, and right ventricular hypertrophy (RVH) can be determined by the ratio of the weight of the right ventricular (RV) free wall to the sum of the left ventricular and septal (LV+S) walls. Lung tissue sections can be stained with alpha smooth muscle actin and von willebrand factor to identify vascular smooth muscle vessels and endothelium respectively.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of hypertension. A subject can be male or female.

A subject can be one who has been previously diagnosed with or identified as suffering from or having a condition in need of treatment (e.g. hypertension) or one or more complications related to such a condition, and optionally, have already undergone treatment for hypertension or the one or more complications related to hypertension. Alternatively, a subject can also be one who has not been previously diagnosed as having hypertension or one or more complications related to hypertension. For example, a subject can be one who exhibits one or more risk factors for hypertension or one or more complications related to hypertension or a subject who does not exhibit risk factors.

A "subject in need" of treatment for a particular condition can be a subject having that condition, diagnosed as having that condition, or at risk of developing that condition.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to e.g., GDF-15.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. hypertension. The term "treating" includes reducing or alleviating at least one adverse effect or symptom of a condition, disease or disorder associated with hypertension. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating hypertension or fibrosis in a subject in need of treatment thereof, the method comprising administering an inhibitor of GDF-15; TGFβ1; and/or TGFβ3 to the subject.
2. The method of paragraph 1, wherein the hypertension is pulmonary arterial hypertension (PAH).
3. The method of any of paragraphs 1-2, wherein the subject is a subject having or diagnosed as having pulmonary arterial hypertension (PAH).
4. The method of paragraph 1, wherein the fibrosis is fibrosis associated with a disease or condition selected from the group consisting of:

emphysema; COPD; interstitial lung disease and pulmonary fibrosis; idiopathic pulmonary fibrosis; scleroderma lung disease; interstitial or pulmonary vascular disease; bleomycin induced lung injury; pulmonary fibrosis due to exposure to chemotherapeutic drugs (methotrexate, cyclophosphamide) or other toxins; chronic lung disease associated with prematurity, a.k.a., bronchopulmonary dysplasia; pulmonary fibrosis or interstitial lung disease associated with exposure to antiarrhythmic drugs (e.g. amiodarone); and interstitial lung disease associated with exposure to asbestos, silica, or grain.
5. The method of paragraph 1 or 3, wherein the subject is a subject having or diagnosed as having a disease or condition selected from the group consisting of:
emphysema; COPD; interstitial lung disease and pulmonary fibrosis; idiopathic pulmonary fibrosis; scleroderma lung disease; interstitial or pulmonary vascular disease; bleomycin induced lung injury; pulmonary fibrosis due to exposure to chemotherapeutic drugs (methotrexate, cyclophosphamide) or other toxins; chronic lung disease associated with prematurity, a.k.a., bronchopulmonary dysplasia; pulmonary fibrosis or interstitial lung disease associated with exposure to antiarrhythmic drugs (e.g. amiodarone); and interstitial lung disease associated with exposure to asbestos, silica, or grain.
6. The method of any of paragraphs 1-5, wherein the inhibitor inhibits TGFβ1.
7. The method of any of paragraphs 1-5, wherein the inhibitor inhibits TGFβ3.
8. The method of any of paragraphs 1-7, wherein the inhibitor inhibits TGFβ1 and TGFβ3.
9. The method of any of paragraphs 1-8, wherein the inhibitor inhibits GDF15.
10. The method of paragraph 9, wherein the inhibitor further inhibits TGFβ1 and/or TGFβ3.
11. The method of any of paragraphs 1-5, wherein the inhibitor is specific for GDF15.
12. The method of any of paragraphs 1-5, wherein the inhibitor is specific for TGFβ1.
13. The method of any of paragraphs 1-5, wherein the inhibitor is specific for TGFβ3.
14. The method of any of paragraphs 1-13, wherein the inhibitor is an antibody reagent or ligand trap.
15. The method of paragraph 14, wherein the ligand trap is a TGFβ-1/3 GDF-15 ligand trap.
16. The method of paragraph 15, wherein the ligand trap is TGFBRII-Fc.
17. The method of any of paragraphs 1-16, wherein the subject has scleroderma or connective tissue disease associated with PAH (APAH-CTD).
18. The method of any of paragraphs 1-17, wherein the subject is determined to have an increased level of GDF-15, TGFβ1, and/or TGFβ3 relative to a control.
19. The method of paragraph 18, wherein the subject is determined to have an increased level of GDF-15, TGFβ1, and/or TGFβ3 relative to the average level of GDF-15, TGFβ1, and/or TGFβ3 in subjects having PAH but not showing symptoms of scleroderma or APAH-CTD.

EXAMPLES

Example 1

Figure 1B:
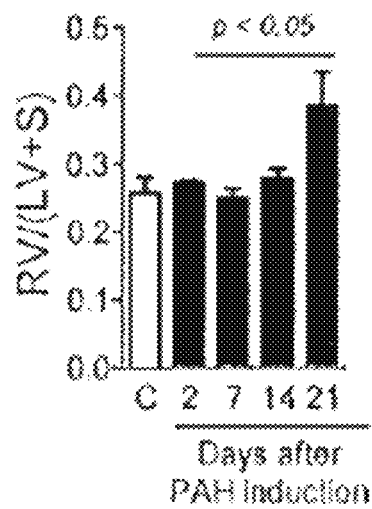
Figure 1C:
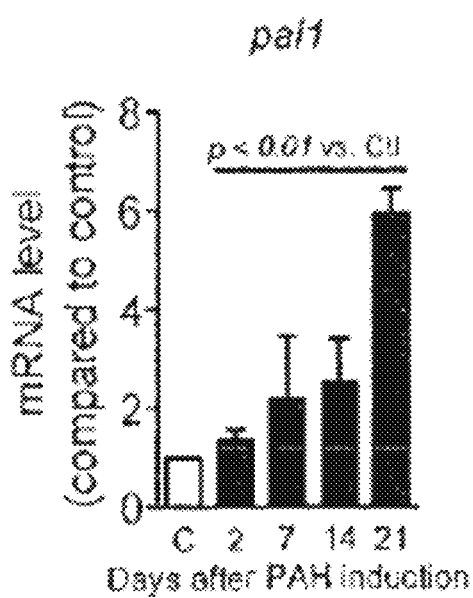
Figure 1D:
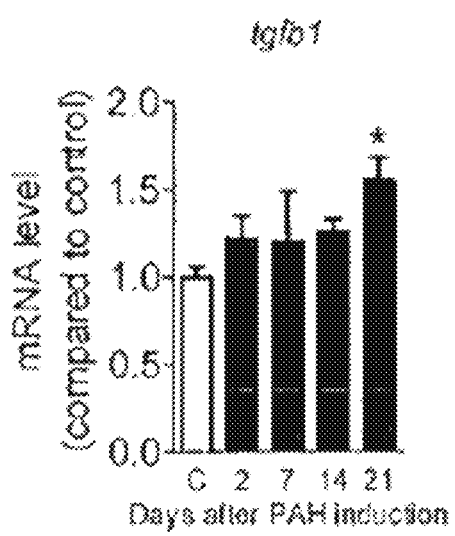
Figure 1E:
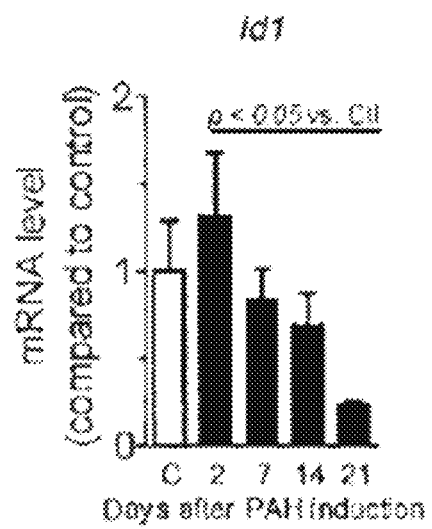
Figure 1F:
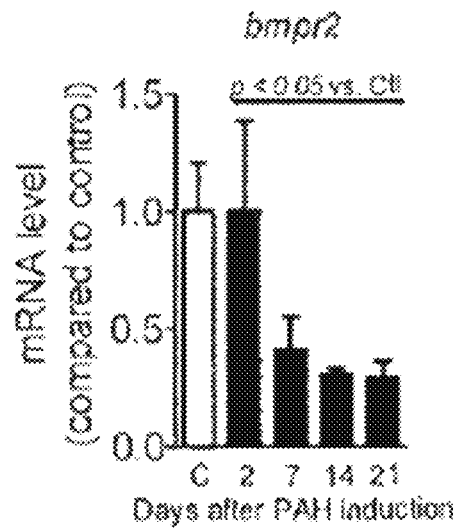
Figure 1G:
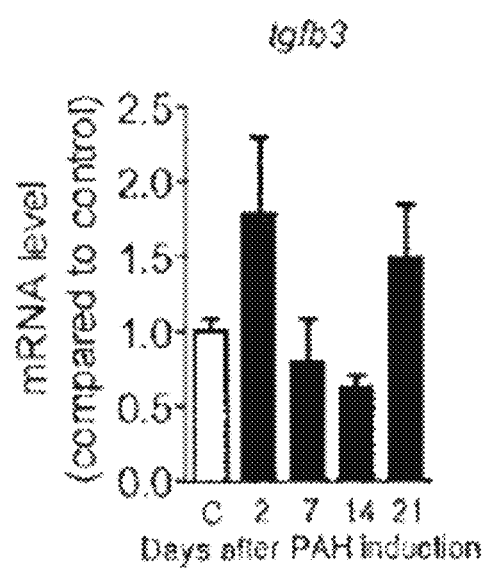
Figure 1H:
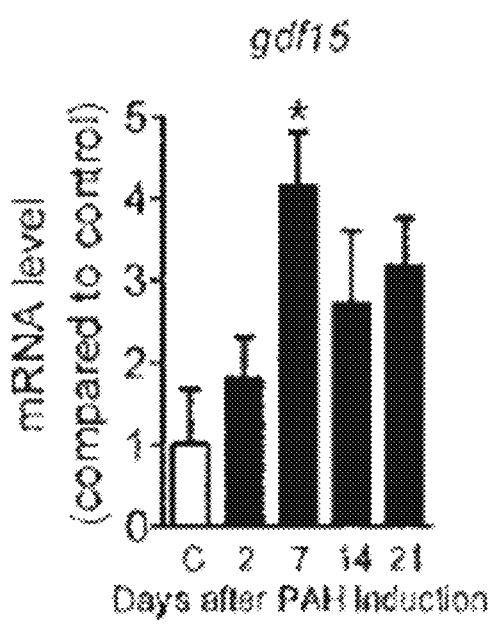

Pulmonary hypertension was induced by treating rats with monocrotaline (MCT). Changes in right ventricular systolic pressure (RVSP, FIG. 1A) and right ventricular hypertrophy (RVH, FIG. 1B) were measured at various intervals after treatment of Sprague Dawley rats with MCT (40 mg/kg SC). RVSP was measured by right ventricular catheterization, and RVH was determined by the ratio of the weight of the right ventricular (RV) free wall to the sum of the left ventricular and septal (LV+S) walls (n=3 per time point). Quantitative RT-PCR of lungs of MGT-treated rats revealed increased TGF-β signaling, reflected by the elevated PAI-1 (FIG. 1C) and TGFb1 transcription activity (FIG. 1D). Impaired BMP signaling activity as shown by decreased ld1 (FIG. 1E) and BMPR2 (FIG. 1F) mRNA levels. Expression of TGFb3 remained unaffected in lungs of MGT-treated rats (FIG. 1G). GDF15 levels were elevated in lungs of MGT-treated rats (FIG. 1H). * p<0.05 and ** p<0.01 compared to control rats.

RNA-Seq was used as a unbiased approach to identify novel pathogenetic target for experimental PAH. GDF15 is the most up-regulated ligand in TGFb superfamily in lungs of MCT-treated rats (Table 1).

Figure 2A:
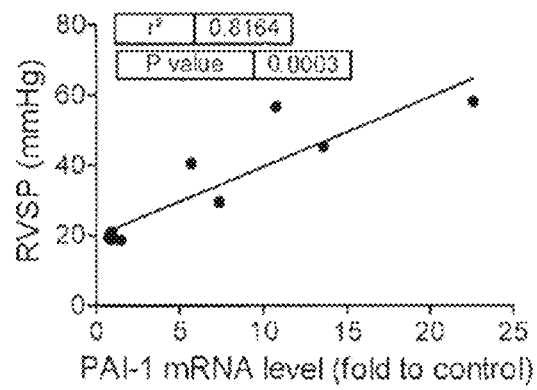
FIGS. 2A-2D demonstrate a correlation between changes in TGF-β and BMP signaling activity and disease severity in MGT-treated rats. Increased levels of PAI-1 (FIG. 2A) correlated directly with the degree of PH based on RVSP. In contrast, decreased expression of transcriptional target ld1 (FIG. 2B) and Bmpr2 (FIG. 2C) were observed, with levels which both correlated inversely with RVSP. There is no correlation between expression of TGFb1 and phenotypes in experimental PAH (FIG. 2D).
Figure 2B:
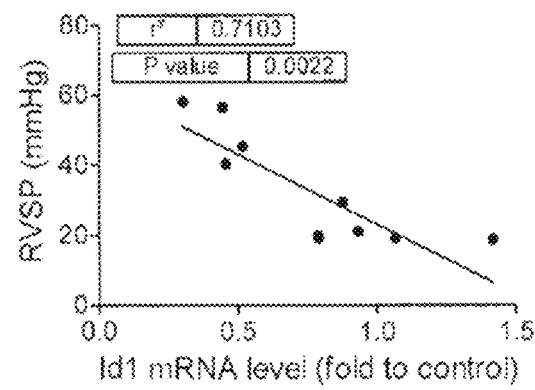
Figure 2C:
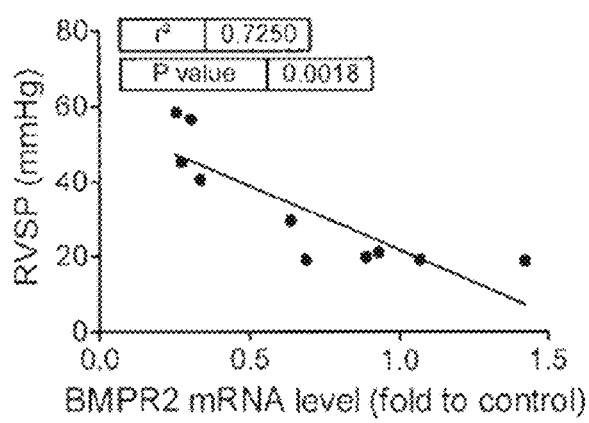
Figure 2D:
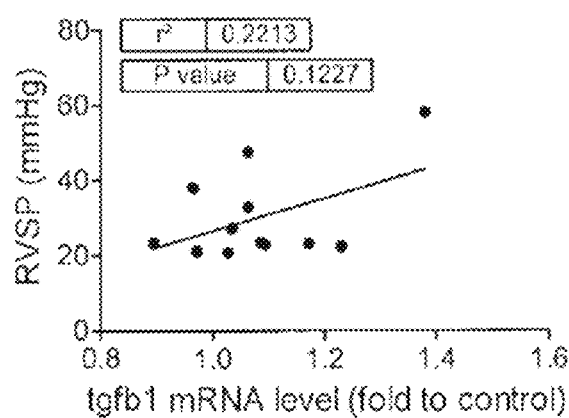

Increased levels of PAI-1 (FIG. 2A) correlated directly with the degree of PH based on RVSP. In contrast, decreased expression of transcriptional target ld1 (FIG. 2B) and Bmpr2 (FIG. 2C) were observed, with levels which both correlated inversely with RVSP. There is no correlation between expression of TGFb1 and phenotypes in experimental PAH. GDF15 protein expression co-localized to endothelium of pulmonary vasculature and CD68-positive cells in lungs of MGT-treated rats (data not shown).

Figure 3A:
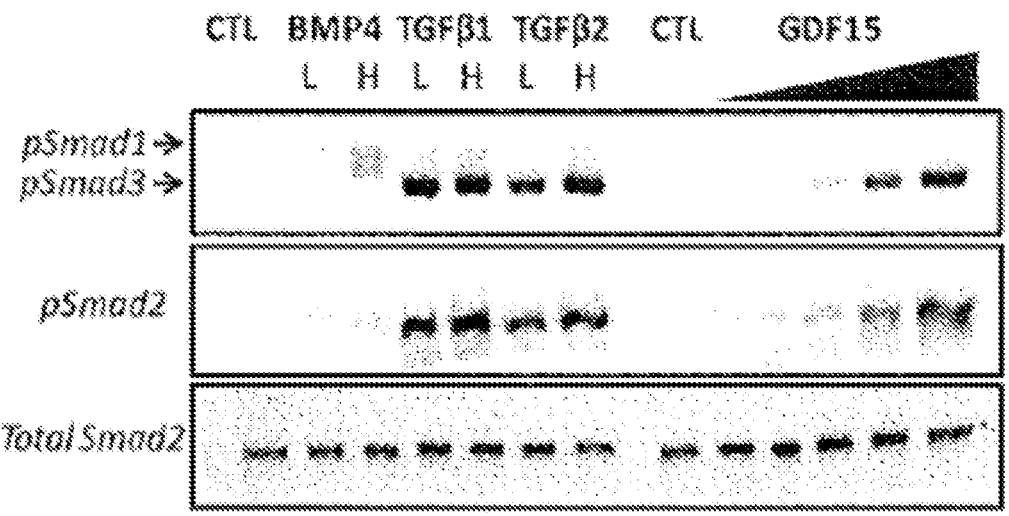
FIGS. 3A-3E demonstrate that TGFBRII-Fc is a selective ligand trap against TGFβ1, and TGFβ3, but not TGFβ2 in vitro. TGFb1, 2, and 3 elicited signaling in human pulmonary artery smooth muscle cells (PASMC, FIG. 3A), and to a substantially lesser degree in human pulmonary microvascular endothelial cells (PMVEC, FIG. 3B). Cultured vascular cells were deprived of serum and incubated with BMP4, BMP9, TGFβ1, TGFβ2, and TGFβ3, at various concentrations for 30 minutes. Western blot (FIG. 3C) and qPCR (FIG. 3D-3E) were performed to determine the impact of TGFBRII-Fc on signaling activity in vitro.
Figure 3B:
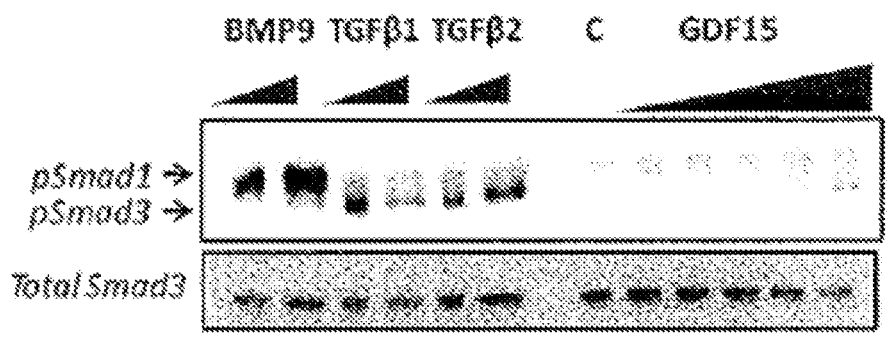

Exogenous GDF15 elicited potent TGFb signaling activity in human pulmonary artery smooth muscle cells (PASMC, FIG. 3A), but not in human pulmonary microvascular endothelial cells (PMVEC, FIG. 3B). Cultured vascular cells were deprived of serum and incubated with BMP4, BMP9, TGFβ1, TGFβ2, TGFβ3, and GDF15 ligands at various concentrations for 30 minutes.

Figure 3C:
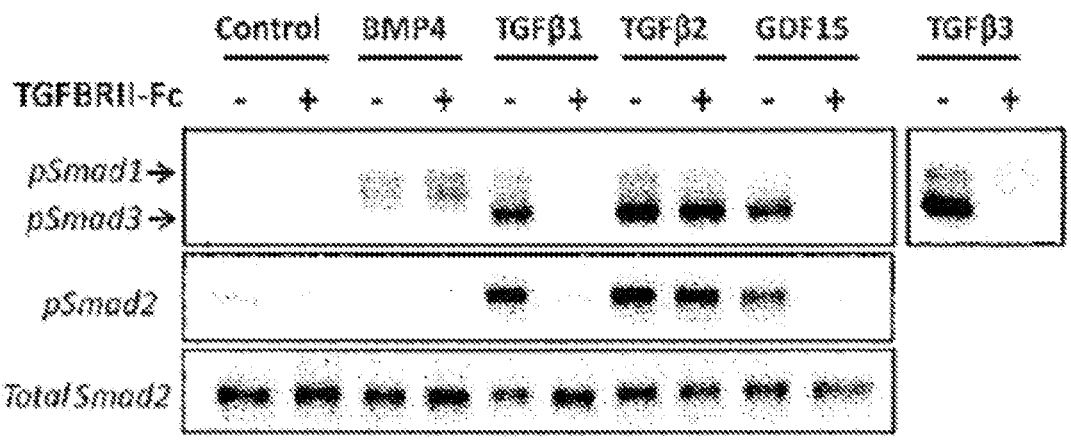
Figure 3D:
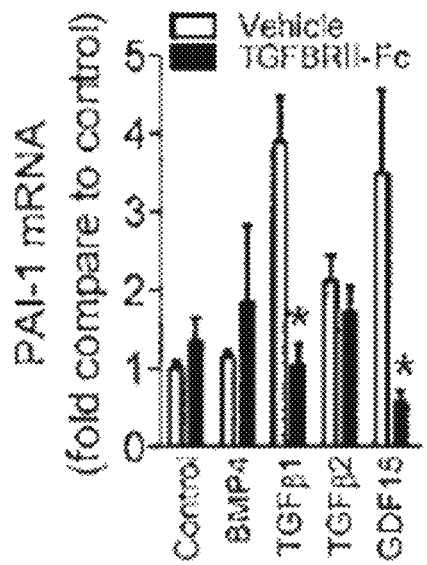
Figure 3E:
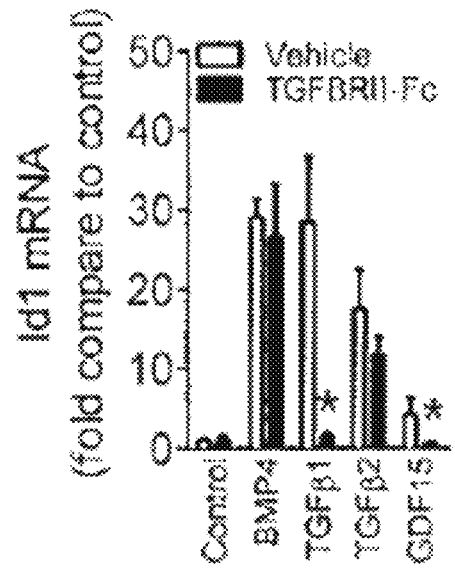

Western blot (FIG. 3C) and qPCR (FIGS. 3D and 3E) were performed to determine the impact of TGFBRII-Fc modulate signaling activity in vitro. TGFBRII-Fc was found to be a selective ligand trap against TGFβ1, TGFβ3, and GDF15 in vitro.

TGFBRII-Fc Attenuates Right Ventricular Systolic Pressure (RVSP), Right Ventricular Hypertrophy and Vascular Remodeling.

Figure 4A:
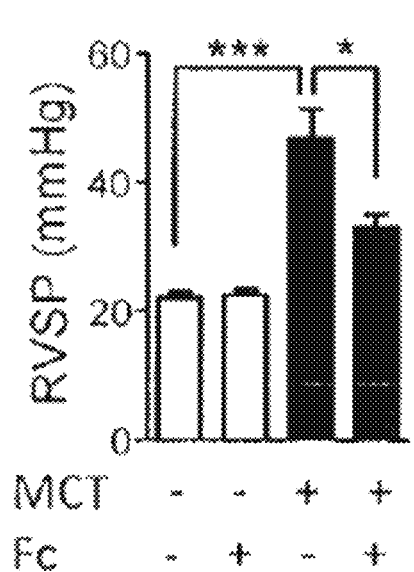
FIGS. 4A-4M demonstrate that TGFBRII-Fc attenuates right ventricular systolic pressure (RVSP), right ventricular hypertrophy and vascular remodeling. Three weeks following treatment with MCT with or without varying doses of TGFBRII-Fc (15 mg/kg, twice per week), rats were analyzed in a blinded fashion by catheterization under anesthesia with pentobarbital and intratracheal intubation to determine RVSP (FIG. 4A) and euthanized. The degree of RVH was assessed in a blinded fashion based on measurement of Fulton's ratio (RV/(LV+S), FIG. 4B). Values are represented as mean±SEM, n=6-8,  $p<0.01$ and * $p<0.001$ compared to control rats. mRNA levels of tgfb1 (FIG. 4C), pai1 (FIG. 4D) il6 (FIG. 4E), il1b (FIG. 4L), and icam (FIG. 4L) were determined. Values are represented as mean±SEM, n=3-5, * $p<0.05$ and  $p<0.01$ compared to control. Muscularization of distal intra-acinar vessels (10-50 (.lm diameter) was quantified, and the percentage of nonmuscular, partially muscularized, and fully (circumferentially) muscularized vessels was calculated (FIG. 4F). TGFBRII-Fc treatment (15 mg/kg twice weekly) significantly reduced the percentage of fully muscularized vessels, and caused a trend towards reduced medial wall thickness index. Values are represented as mean±SEM, n=89-127 vessels per treatment group from 6-8 rats each, p values as shown. Treatment with TGFBRII-Fc following establishment of PH is associated with partial rescue of PH and mortality. After treatment with MCT (40 mg/kg SC), rats were treated in a delayed fashion starting on day 17 after the establishment of PH with TGFBRII-FC (15 mg/kg three times weekly). Kaplan-Meier analysis (FIG. 4G) revealed an improved survival in the TGFBRII-Fc-treated group as compared to rats treated with vehicle (n=18 per group). Among surviving animals at 35 days, there was significantly decreased RVSP among animals treated with TGFBRII-Fc (FIG. 4H), but no significant difference in RVH FIG. 4I). Values shown are mean±SEM, n=8-11 per group,  $p<0.01$ compared to control. TGFBRII-Fc treatment attenuated pulmonary vascular remodeling in rats with established phenotypes (FIG. 4J). TGBRII-Fc decreased the percentage of fully muscularized vessels (10-50 μm diameter), and medial wall thickness, calculated as (external diameter−internal diameter)/external diameter×100. n=89-127 vessels per treatment group from 6-8 rats each (FIG. 4J-4K).
Figure 4B:
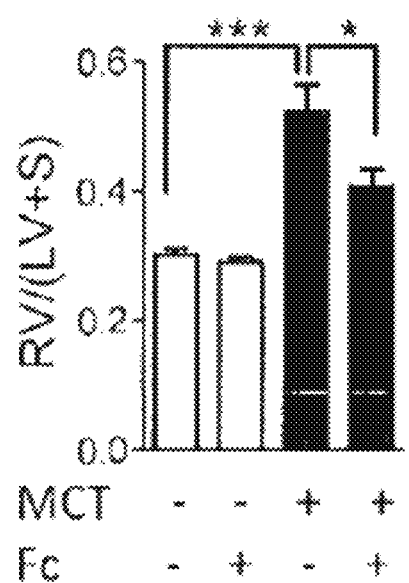
Figure 4C:
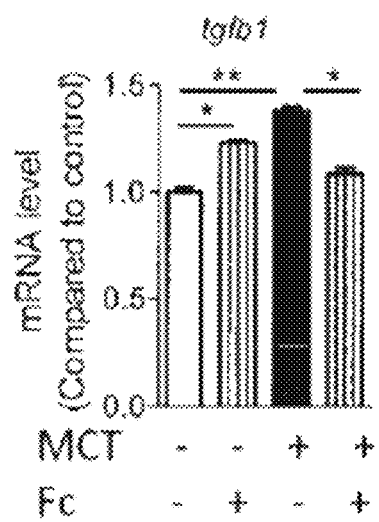
Figure 4D:
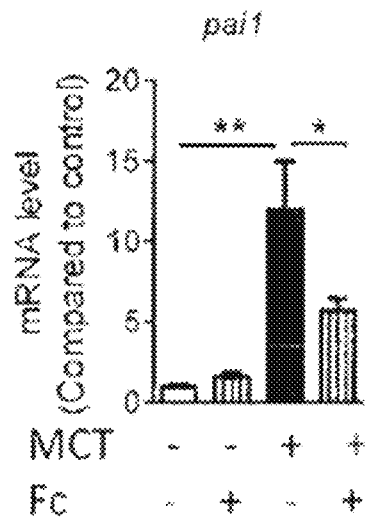
Figure 4E:
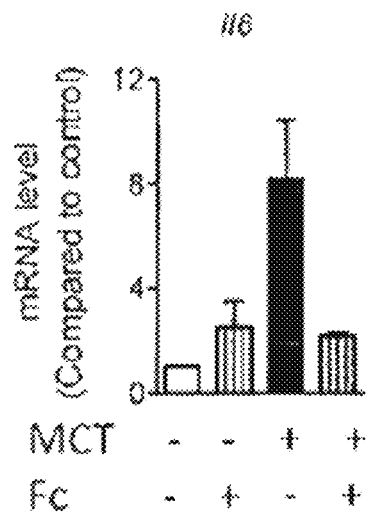
Figure 4F:
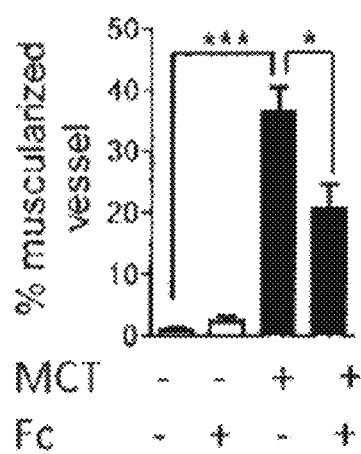
Figure 4G:
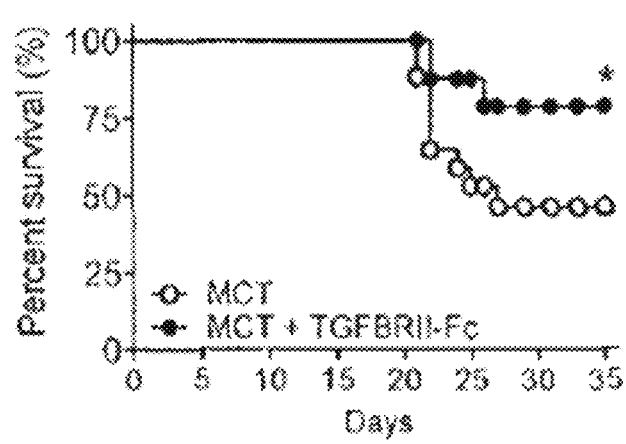
Figure 4H:
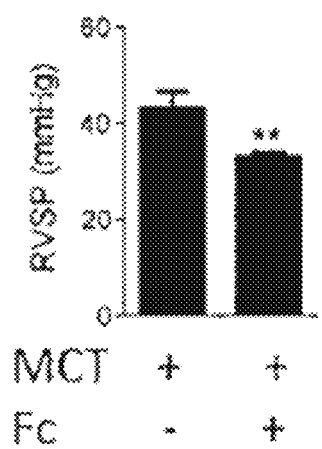
Figure 4I:
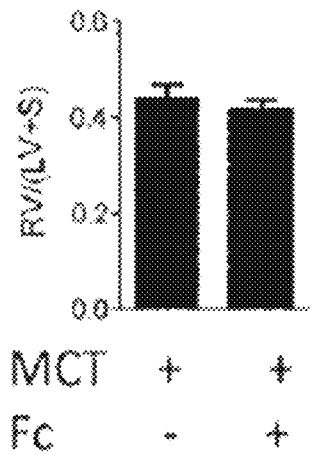
Figure 4J:
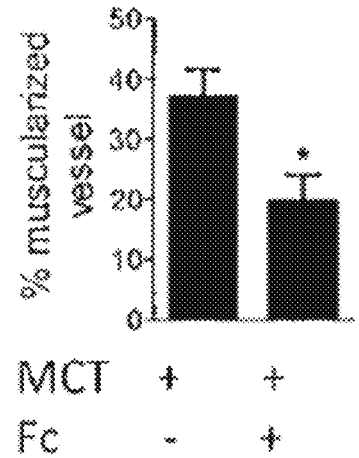
Figure 4K:
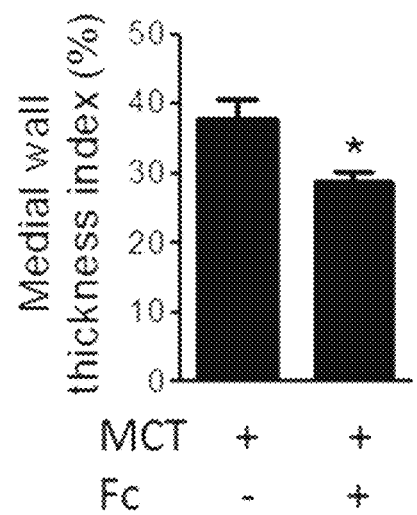
Figure 4L:
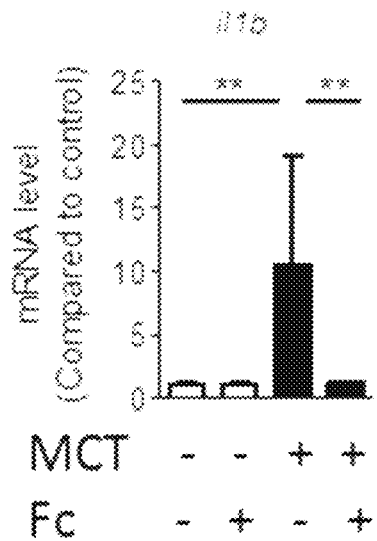
Figure 4M:
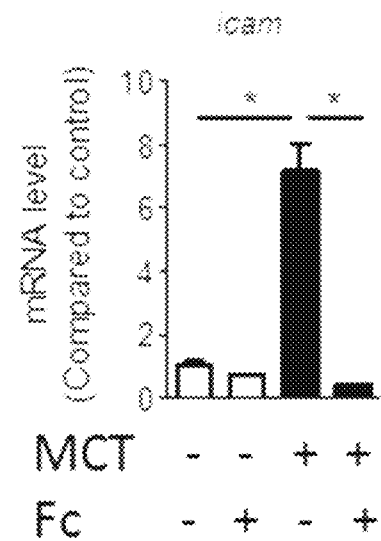

Three weeks following treatment with MCT with or without varying doses of TGFBRII-Fc (15 mg/kg, twice per week), rats were analyzed in a blinded fashion by catheterization under anesthesia with pentobarbital and intratracheal intubation to determine RVSP (FIG. 4A) and euthanized. The degree of RVH was assessed in a blinded fashion based on measurement of Fulton's ratio (RV/(LV+S), FIG. 4B). Values are represented as mean±SEM, n=6-8, p<0.01 and *p<0.001 compared to control rats. mRNA levels of tgfb1 (FIG. 4C), pail (FIG. 4D) and il6 (FIG. 4E) were determined. Values are represented as mean±SEM, n=3-5, *p<0.05 and  p<0.01 compared to control. Lung tissue sections were stained with alpha smooth muscle actin and von willebrand factor to identify vascular smooth muscle vessels and endothelium respectively (data not shown). Muscularization of distal intra-acinar vessels (10-50 (.lm diameter) was quantified, and the percentage of nonmuscular, partially muscularized, and fully (circumferentially) muscularized vessels was calculated (FIG. 4F). TGFBRII-Fc treatment (15 mg/kg twice weekly) significantly reduced the percentage of fully muscularized vessels, and caused a trend towards reduced medial wall thickness index. Values are represented as mean±SEM, n=89-127 vessels per treatment group from 6-8 rats each, p values as shown. Treatment with TGFBRII-Fc following establishment of PH is associated with partial rescue of PH and mortality. After treatment with MCT (40 mg/kg SC), rats were treated in a delayed fashion starting on day 17 after the establishment of PH with TGFBRII-FC (15 mg/kg three times weekly). Kaplan-Meier analysis (FIG. 4G) revealed an improved survival in the TGFBRII-Fc-treated group as compared to rats treated with vehicle (n=18 per group). Among surviving animals at 35 days, there was significantly decreased RVSP among animals treated with TGFBRII-Fc (FIG. 4H), but no significant difference in RVH U). Values shown are mean±SEM, n=8-11 per group,  $p<0.01$ compared to control. TGFBRII-Fc treatment attenuated pulmonary vascular remodeling in rats with established phenotypes.

Efficacy of TGFBRII-Fc in Murine Model of PAH.

Figure 5A:
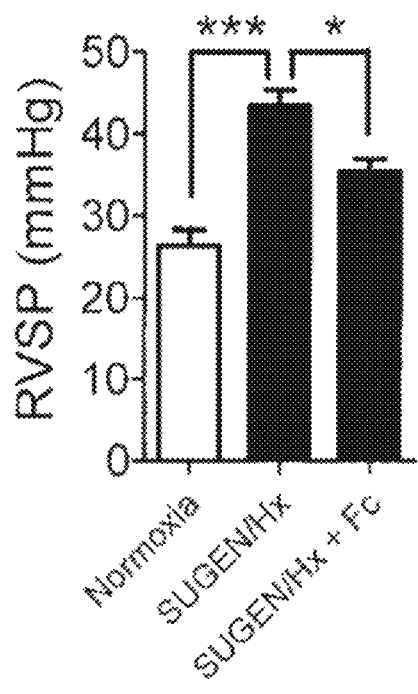
FIGS. 5A-5B demonstrate the efficacy of TGFBRII-Fc in murine model of PAH. Mice were treated with VEGFR blocker (SUGEN) and exposed to hypoxia for 3 weeks. TGFBRII-Fc treatment (15 mg/kg, three times per week) reduced RVSP (FIG. 5A) and prevented right ventricular hypertrophy (FIG. 5B).
Figure 5B:
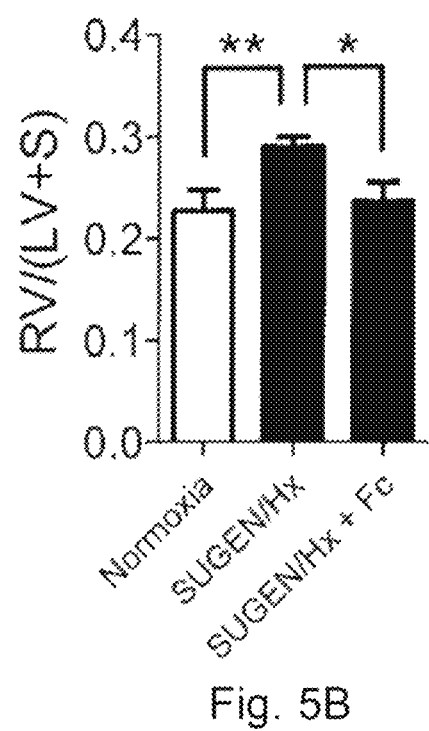

Mice were treated with VEGFR blocker (SUGEN) and exposed to hypoxia for 3 weeks. TGFBRII-Fc treatment (15 mg/kg, three times per week) reduced RVSP and prevent right ventricular hypertrophy (FIGS. 5A-5B).

Transgenic Mice are Used to Ascertain the Pathogenetic Role of GDF15.

GDF15 knockout mice are protected against SUGEN/Hypoxia-induced PAH (FIGS. 6A-6D). $p<0.01$ and* $p<0.001$ as shown.

Figure 7B:
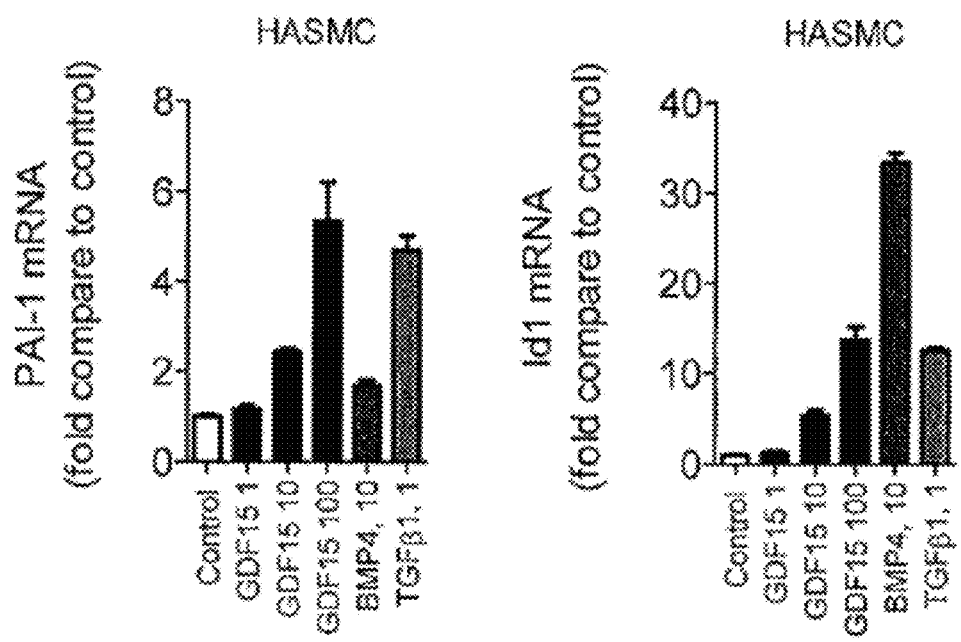

Consistent with the data in pulmonary vascular smooth muscle cells, GDF15 induced potent TGFb signaling in human aortic smooth muscle cells (HASMC) in vitro. BMP4, TGFb1 and TGFb2 were used as positive controls (FIGS. 7A-7B).

Figure 8A:
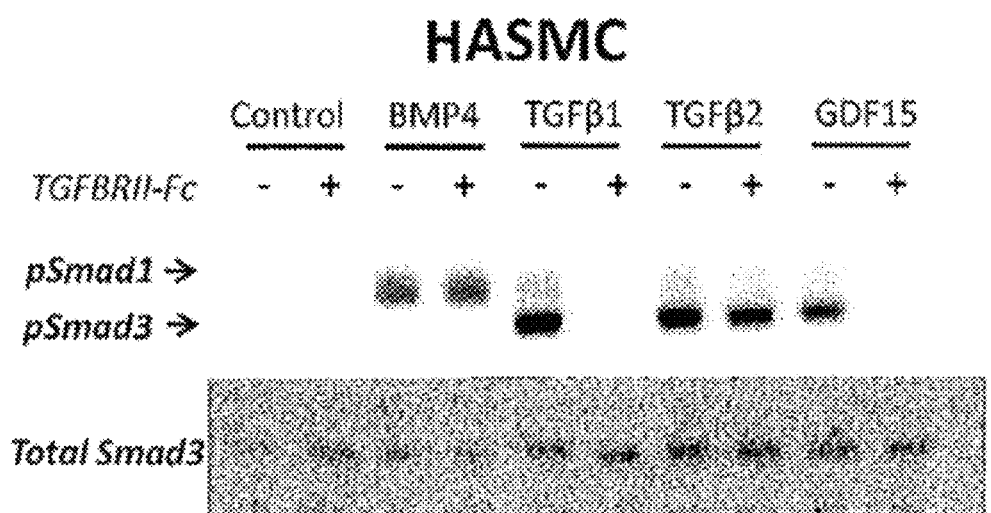
FIGS. 8A-8B demonstrate the selectivity of TGFBRII-Fc in blocking TGFb1-, and TGFb3-, signaling is confirmed in HASMC. * $p<0.05$ and ** $p<0.01$ as indicated.
Figure 8B:
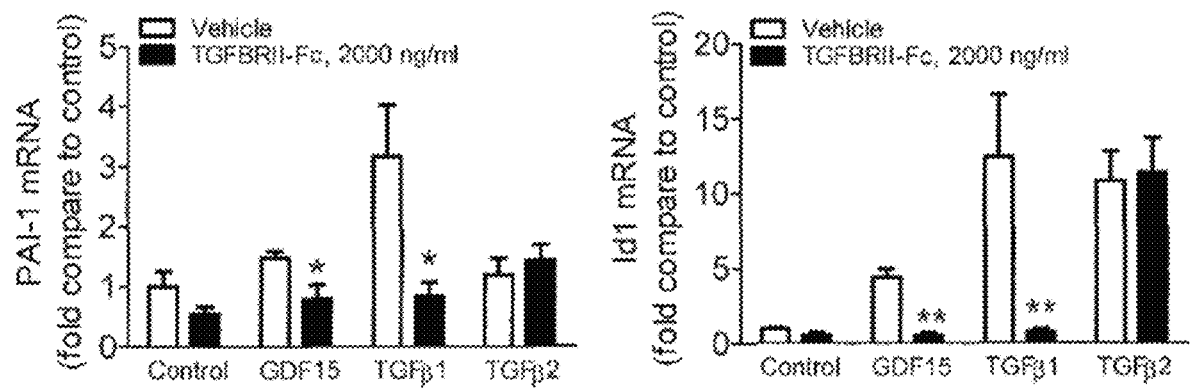
Figure 9:
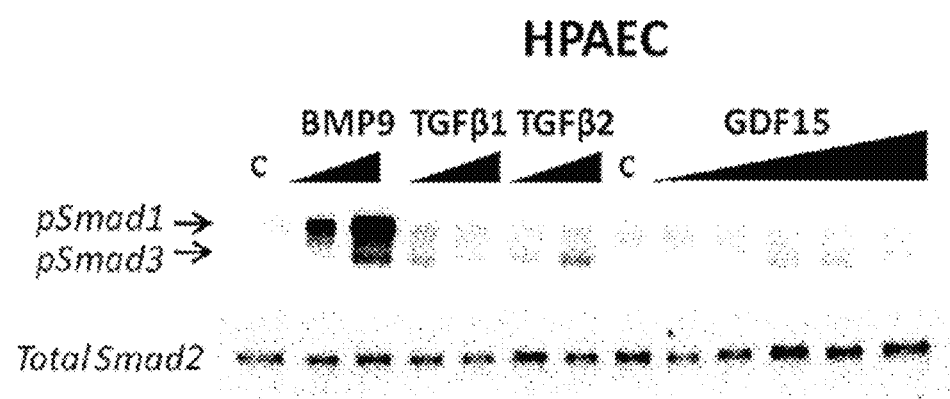
FIG. 9 demonstrates that exogenous GDF15 failed to induce TGFb signaling in human pulmonary artery endothelial cells (HPAEC), consistent with the data in microvascular endothelial cells (HPMVEC).

Selectivity of TGFBRII-Fc in blocking TGFb1-, TGFb3-, and GDF15-induced signaling was confirmed in HASMC (FIG. 8A-8B). *$p<0.05$ and **$p<0.01$ as indicated.

Exogenous GDF15 failed to induce TGFb signaling in human pulmonary artery endothelial cells (HPAEC) (FIG. 7), consistent with the data in microvascular endothelial cells (HPMVEC).

Figure 10A:
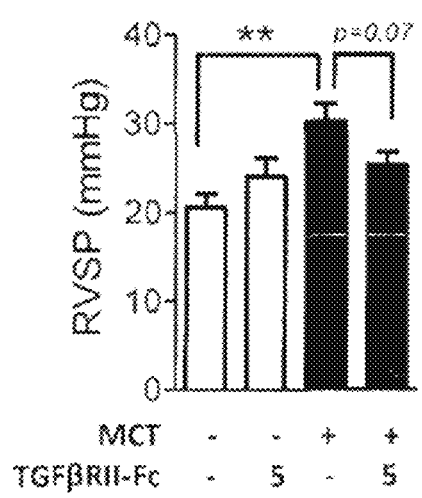
FIGS. 10A-10E demonstrate that low dose of TGFBRII-Fc (5 mg/kg, twice per week) reduced RVSP (FIG. 10A) and right ventricular hypertrophy (FIG. 10B) in MCT-treated rats. Notably, low doses of TGFBRII-Fc treatment significantly prevented pulmonary vascular remodeling in MCT-rats (FIG. 10C-10E).
Figure 10B:
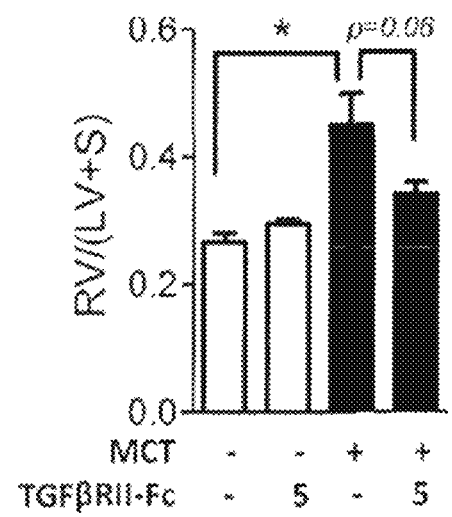
Figure 10C:
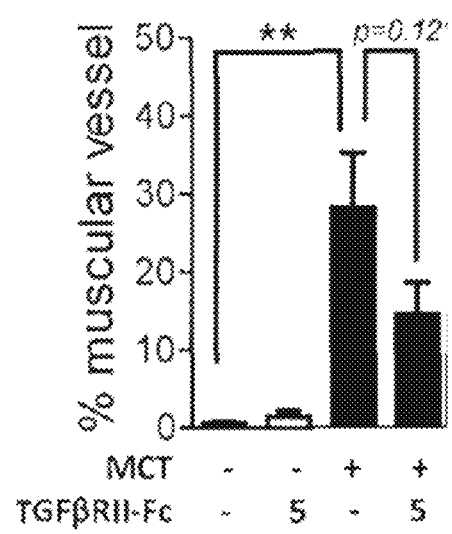
Figure 10D:
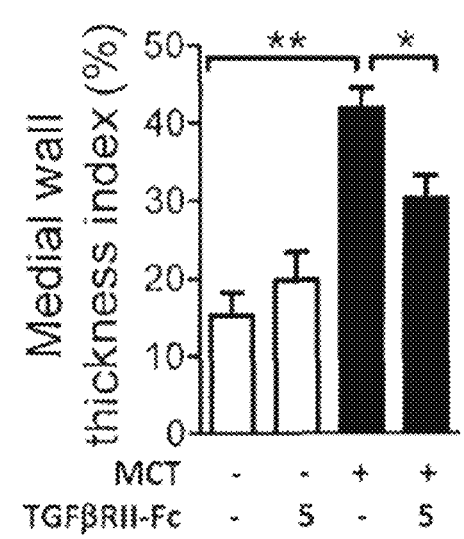
Figure 10E:
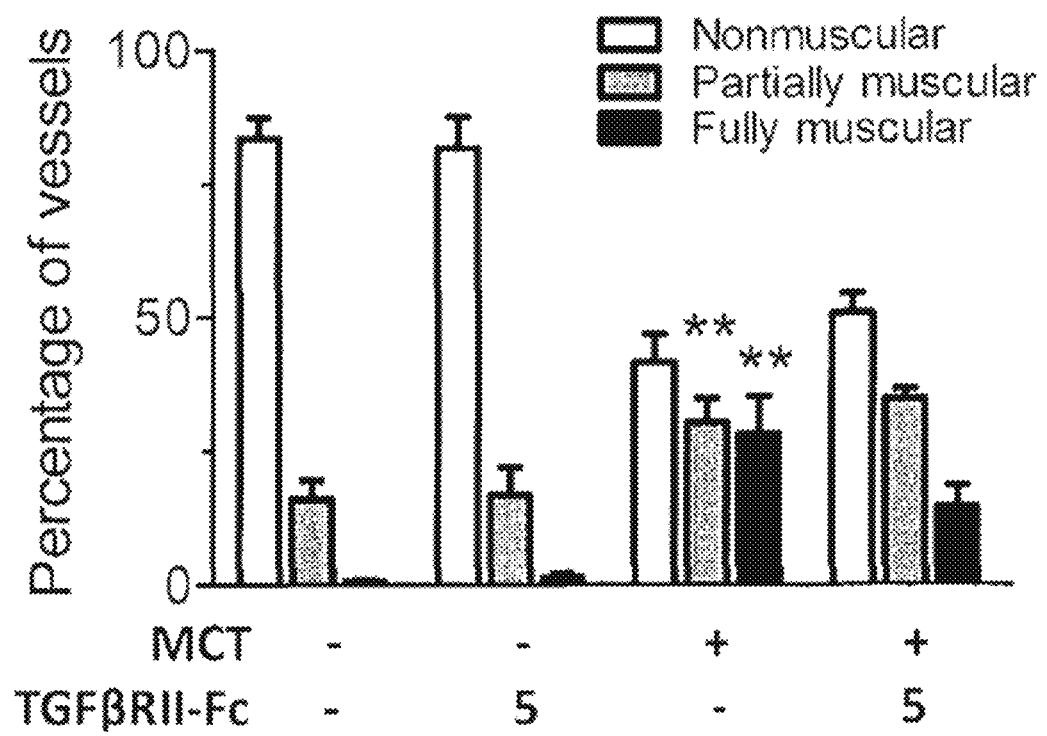
Figure 11:
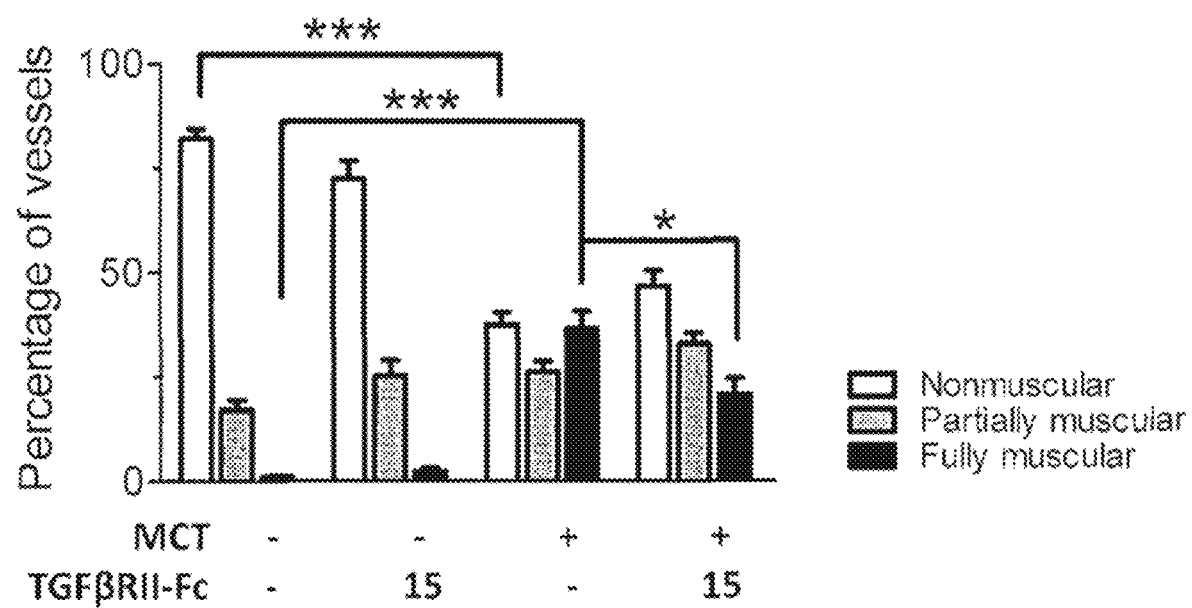
FIG. 11 depicts a graph of the percentage of vessels that were nonmuscular, partially muscular, or fully muscular following treatment with MCT and TGFβRII-Fc.
Figure 12:
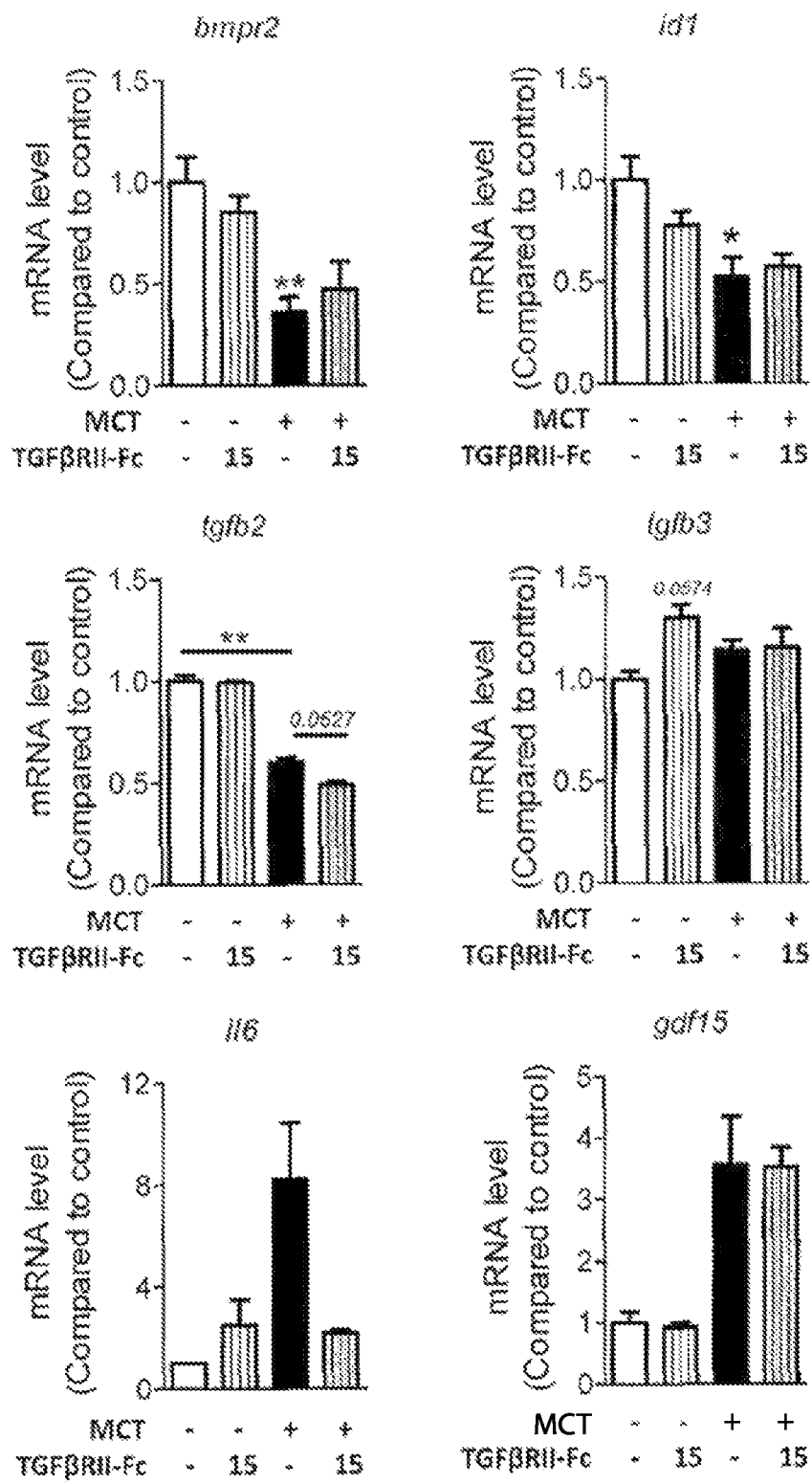
FIG. 12 depicts graphs of the mRNA expression of bmpr2, id1, tgfb2, tgfb3, il6, and gdf15 following treatment with MCT and TGFβRII-Fc.

Low dose of TGFBRII-Fc (5 mg/kg, twice per week) showed a trend reduced RVSP (FIG. 10A) and right ventricular hypertrophy (FIG. 10B) in MGTtreated rats. Notably, low dose of TGFBRII-Fc treatment significantly prevented pulmonary vascular remodeling in MGT-rats.

TABLE 1

RNA-Seq is used as a unbiased approach to identify novel pathogenetic target for experimental PAH. GDF15 is the most up-regulated ligand in TGFb superfamily in lungs of MCT-treated rats.

| | MCTvs PBS Fold Change | p-Value |
|---|---|---|
| Bmpr2 | -1.7 | 0.1563 |
| Bmpr1a | 1 | 0.9321 |
| Tgfbr1 | 1 | 0.7554 |
| Tgfbr2 | 1.2 | 0.5096 |
| Tgfbr3 | -1.4 | 0.1705 |
| Acvr2a | 1 | 1 |
| Acvr2b | -1.2 | 0.5134 |
| Acvrl | 1.1 | 0.8787 |
| Acvrlb | -1.2 | 0.3659 |
| Acvrlc | -1.1 | 0.6498 |
| Bmp1 | 1.1 | 0.7753 |
| Bmp2 | 2.3 | 0.0102 |
| Bmp3 | 1.1 | 0.869 |
| Bmp4 | -1.2 | 0.3078 |
| Bmp5 | 1 | 0.9838 |
| Bmp6 | -1.7 | 0.1181 |
| Bmp7 | -1.8 | 0.4159 |
| Bmp8b | -1.5 | 0.6473 |
| Bmp8a | 1.2 | 0.7278 |
| Bmp10 | -3.8 | 0.2094 |

TABLE 1-continued

RNA-Seq is used as a unbiased approach to identify novel pathogenetic target for experimental PAH. GDF15 is the most up-regulated ligand in TGFb superfamily in lungs of MCT-treated rats.

| | MCTvs PBS Fold Change | p-Value |
|---|---|---|
| Bmp15 | -1.3 | 0.7292 |
| Tgfb1 | 1.5 | 0.0678 |
| Tgfb2 | -1 | 0.6544 |
| Tgfb3 | 1.3 | 0.1295 |
| Inha | 1.2 | 0.7111 |
| Inhba | 1.9 | 0.5848 |
| Inhbb | -1.5 | 0.0472 |
| Cxcl10 | 2.8 | 0.0959 |
| IL1a | -1.2 | 0.7093 |
| IL1b | -1 | 0.5274 |
| Tnf | 1 | 0.5065 |
| Ccl2 | 1.3 | 0.7985 |
| Spp1 | 6.9 | 0.5074 |
| Vegfa | -1.5 | 0.0406 |
| Vegfb | -1.2 | 0.2886 |
| Vegfc | 1 | 0.8721 |
| Gdf2 | -1.4 | 0.5169 |
| Gdf3 | 1.5 | 0.8954 |
| Gdf5 | -2.1 | 0.9941 |
| Gdf6 | -1 | 1 |
| Gdf7 | -2.1 | 0.9993 |
| Mstn | -4.6 | 0.3541 |
| Gdf11 | 1.5 | 0.627 |
| Gdf15 | 3.3 | 0.0002 |

Example 2: A Selective TGF-β Ligand Trap Ameliorates Pulmonary Arterial Hypertension Transforming Growth Factor-β (TGF-β) ligands serve as critical regulators of development and tissue homeostasis, signaling via type I and type II serine-threonine kinase receptors to modulate transcriptional programs. An excess of TGF-β signaling and associated transcriptional and remodeling activity have been implicated in the pathogenesis of pulmonary arterial hypertension (PAH), based on immunohistological and gene expression studies, and the ability of TGF-β type I receptor (ALK5) inhibitors to attenuate experimental PAH. However, therapeutic potential has been limited by cardiovascular and systemic toxicity associated with broad inhibition of TGF-β ligands. In the present study, we investigated whether a selective TGF-β1/3 ligand trap, TGFBRII-Fc could impact experimental PAH and pulmonary vascular remodeling. Treatment with TGFBRII-Fc attenuated SMAD2 phosphorylation, normalized expression of TGF-β transcriptional target PAI-1, and mitigated PAH and pulmonary vascular remodeling in monocrotaline-treated rats and SUGEN-hypoxia-treated mice. Administration of TGFBRII-Fc to monocrotaline-treated rats with established PAH improved pulmonary pressures, survival and remodeling. Importantly, no cardiac structural or valvular abnormalities were found in association with TGFBRII-Fc treatment. Collectively, our data indicate that a selective TGF-β ligand trap can be effective and tolerable strategy for correcting TGFβ-mediated pulmonary vascular remodeling and PH.

Pulmonary arterial hypertension (PAH) is a highly morbid condition characterized by elevated pulmonary vascular resistance (PVR) and arterial pressures, driven by a progressive pulmonary vasculopathy. which leads to right ventricular hypertrophy (RVH), and frequently, right ventricular failure and death.[1,2] The pulmonary vascular lesions of PAH include medial hypertrophy, neointimal and obstructive lesions consisting of hyperproliferative myofibroblast and endothelial lineages, and multichanneled plexiform lesions that are pathognomic in this diseas. Idiopathic and hereditary forms of PAH are associated with heterozygous mutations in BMPR2 encoding the bone morphogenetic protein (BMP) type II receptor (BMPRII),[3,4] a member of the transforming growth factor-β (TGF-β) signaling family with numerous important functions in the cell physiology of the vascular endothelium and smooth muscle as well as other tissues.[5-8] The TGF-β signaling family includes more than 30 ligands, including BMPs, TGF-β, Activins, and growth and differentiation factors (GDFs), each of which act as multifunctional cytokines with potentially important contributions to vascular homeostasis and disease.[9-11]

While PAH-associated mutations of BMPR2 result in loss of BMP signaling function, it has been long observed that lung tissues from human IPAH are marked by enhanced activity of the TGF-β pathway.[12] In fact, multiple animal models of pulmonary hypertension, including those induced by hypoxia, monocrotaline-induced injury, or infection with schistosomiasis, have shown similar evidence of elevated TGF-β ligand expression and downstream transcriptional activity.[13-16] Enhanced TGF-β signaling in these models was associated with PAH accompanied by smooth muscle hypertrophy, perivascular fibrosis and extracellular matrix remodeling, all of which could be ameliorated with pharmacologic inhibitors of the TGF-β type I receptor kinases ALK5,[13,17] which also inhibited closely related homologous Activin and Nodal receptors ALK4 and ALK7. Limiting the therapeutic potential of this strategy, however, was the observation that potent inhibition of ALK4/5/7 via small molecules led to significant cardiovascular toxicity, in the form of hemorrhagic valve necrosis, as well as physeal hypertrophy and dysplasia in the femoral tibial joints of adolescent animals.[18] It was shown that a neutralizing monoclonal antibody, 1D11, which recognizes TGF-β ligands TGF-β1, 2, and 3 was also able to attenuate pulmonary hypertension in a monocrotaline model of PAH in rats.[1,19] However, the use of a similar pan-TGF-β neutralizing antibody in man, fresolimumab has been associated with dose-related side effects including skin rashes and lesions, epistaxis, gingival bleeding and fatigue.[20] It is presently unclear if any of the individual ligands of the TGF-β family may be primarily responsible for these effects. In the present study, we sought to determine the effects of selective TGF-β ligand-blockade in pulmonary vascular remodeling using a recombinant TGFBRII-Fc extracellular domain fusion protein. This ligand trap binds TGF-β1 and β3, but does not bind TGF-β2, which requires an interaction with TGFBRIII (betaglycan). As described herein such a strategy can ameliorate aspects of pulmonary vascular remodeling and PAH in animal models, without incurring toxic liabilities due to the inhibition of TGF-β2, which is known to be unique among TGF-β ligands for its essential role in cardiac valve morphogenesis, and in regulating endothelial and epithelial-to-mesenchymal transition in a variety of tissues.[21-29]

Materials and Methods

Cell culture. Human pulmonary artery smooth muscle cells (HPASMC) were purchased from Lonza (CC-2581) and maintained in SmGM-2 medium supplemented with commercially available growth factor (CC-3182). CAGA-Luc and BRE-Luc cells were maintained in DMEM supplemented with 10% FBS. Cells were incubated with 0.5% FBS without growth supplements to achieve quiescence before experimental stimuli. Where noted, quiescent cells were treated with TGFBRII-Fc (2000 ng/ml) 30 min before experimental stimuli.

Experimental PAH Models.

Adult male Sprague-Dawley rats (150-170 g) and male C57BL/6J mice (20-25 g) were purchased from Charles River Laboratory. All experimental and surgical protocols were approved by Harvard Institutional Animal Care and Use Committee. Animals were housed at 24° C. in a 12-hour light-dark cycle. Food and water were accessible ad libitum. To induce PAH, rats received a single subcutaneous injection of monocrotaline (MCT, 40 mg/kg, Oakwood). Mice received three consecutive weekly subcutaneous injections of VEGF receptor antagonist (SU5416, 20 mg/kg) while being exposed to normobaric hypoxia in a regulated chamber via infusion of $N_2$ gas ($FIO_2$=10%, BioSpherics) for 3 weeks.

Prophylaxis in MCT-Treated Rats.

At 24 hours after administration of MCT, rats were randomized into groups receiving TGFBRII-Fc (5 or 15 mg/kg, twice per week) or vehicle. Rats were treated for 21 days. At day 14, ventricular function and RV remodeling were examined by echocardiogram. At day 21, rats were subjected to invasive hemodynamic and RVH measurements.

Rescue in MCT-Treated Rats.

To test the ability of TGFBRII-Fc to reverse established PAH, rats were chosen at random starting 18 days after MCT exposure to receive TGFBRII-Fc (15 mg/kg, three times per week) or vehicle. Hemodynamics and RVH were examined on day 35.

Prophylaxis in SUGEN/Hypoxia Mice.

At 24 hours after PAH induction, mice were randomized and received TGFBRII-Fc (15 mg/kg, three times per week). At day 21, mice were subjected to hemodynamics and RVH measurements.

Echocardiographic Assessment of LV and RV Function.

Fourteen days following after administration of MCT, rats were anesthetized with 1.5% isoflurane and held in a supine position. A VisualSonics small animal high-frequency ultrasound probe was used to detect pulmonary flow acceleration, right ventricular function and hypertrophy, and left ventricular function. Doppler across the mitral and tricuspid valves was performed to determine if TGFBRII-Fc treatment resulted in valvular regurgitation or structural abnormalities of the valves.

Invasive Hemodynamic Measurements and Assessment of Right Ventricular Hypertrophy.

At specified time points, rats were anesthetized with pentobarbital (50 μg/kg i.p.) and intubated through intratracheally. Rats were mechanically ventilated using a rodent ventilator (TV=8 ml/kg, f=80/min) and invasive hemodynamic measurements of pressure using a fluid-filled catheter through the RV apex, as described previously.[19] Lungs were perfused with PBS and one right lobe was excised and snap frozen for RNA and protein extraction. Lungs were further perfused with 1% paraformaldehyde (PFA) into the pulmonary artery, followed by trachea for 1 minute. Left lobes were embedded in paraffin. To access degree of RVH, the heart was removed and the RV free wall dissected from the left ventricle plus septum (LV+S) and weighted separately. Degree of RVH was determined from the ration RV/(LV+S). The remaining portion of LV and septal wall was embedded in OCT and sectioned. H&E staining was performed to examined the anatomy of mitral valves.

Quantification of vascular remodeling and p-Smad 2 in lung tissues. To determine the degree of pulmonary vascular remodeling, lung tissue sections were stained with smooth muscle α-actin and von Willebrand Factor. Muscularization of distal intra-acinar vessels (10-50 μm diameter) was scored in a blinded fashion as being nonmuscular, partially muscularized, and fully muscularized, and expressed as a percentage of total vessels. For fully muscularized intra-acinar vessels, medial wall thickness was calculated based on the formula: medial thickness–(external diameter–internal diameter)/external diameter×100. Phosphorylation of Smad2 protein in frozen sectioned lung tissues (10 µm) was examined by immunofluorescence staining.

Expression Studies.

Frozen lung samples were homogenized and total RNA extracted using TRIZOL reagent. Reverse transcriptase and quantitative PCR were performed as described. Relative levels of expression of each gene of interest were determined by the Ct method and expressed as a ratio to the expression of β-actin.

Reagents.

Recombinant TGFBRII was expressed as a fusion protein with IgG Fc domain (TGFBRII-Fc) in CHO cells and purified as previously described. Primary antibodies against phosphorylated (p-) Smad3 (p-Smad3), p-Smad1/5, p-Smad2, and total Smad3 were purchased from Cell Signaling. Primary antibodies against smooth muscle α-actin and von Willebrand Factor were purchased from Sigma and Dako, respectively. Recombinant TGFβ-1, TGFβ-2, TGFβ-3 and BMP4 were purchased from R&D.

Statistical analysis. Quantitative analyses of invasive hemodynamic pressure measurements and assessments of RVH and pulmonary vascular remodeling were consistently performed in a manner blinded with respect to treatment groups, with the identities of all animals and tissue samples masked by an individual not involved in the data collection. Data are presented as mean±standard error of measurement (SEM) and compared between groups using the student's T test, with Bonferroni correction for multiple tests, or ANOVA. $P<0.05$ was considered statistically significant.

Results

Figure 13A:
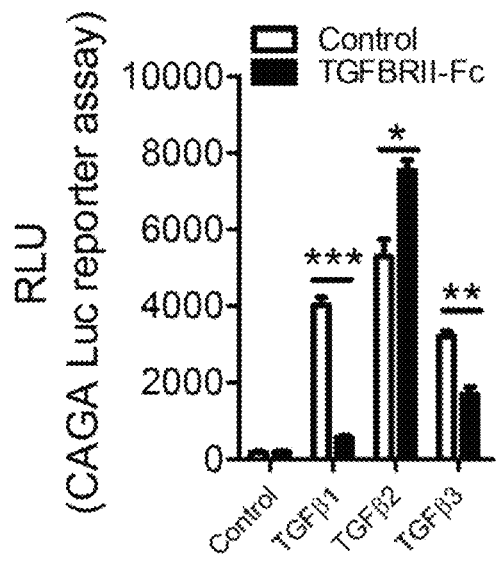
FIGS. 13A-13D demonstrate that TGFRII-Fc selectively inhibits TGFβ1- and TGFβ3-induced signaling. HEK293 cells expressing CAGA-Luc (FIG. 11A) and C2C12 cells expressing BRE-Luc reporter transgene (FIG. 11B) were incubated with TGFBRII-Fc (2000 ng/ml) for 30 min prior to exposing to BMP or TGFβ overnight. Human pulmonary artery smooth muscle cells (HPASMC, c-d) were deprived of serum overnight, pretreated with TGFBRII-Fc (2000 ng/ml), followed by incubation with BMP4 (10 ng/ml), TGFβ1 (1 ng/ml), TGFβ2 (1 ng/ml), or TGFβ3 (1 ng/ml) for 30 min, and analyzed by immunoblot for phosphorylation of Smads 1, 2, and 3 (FIG. 11C) and TGFβ transcriptional target (PAI-1, FIG. 11D). TGFBRII-Fc inhibited signaling via TGF-β1 and TGF-β3, but not TGFβ2. (* $p<0.05$,  $p<0.01$, * $p<0.001$ as indicated).
Figure 13B:
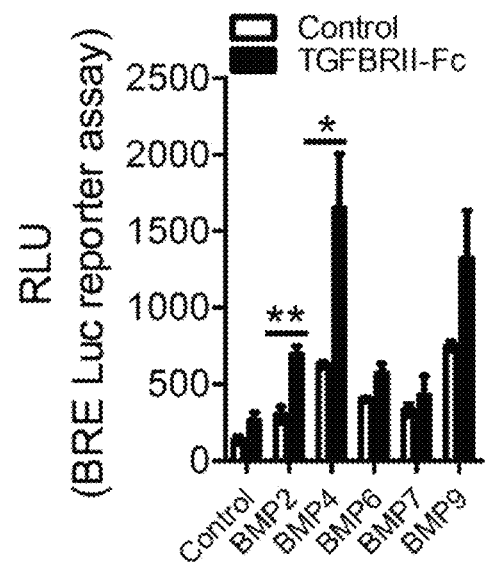
Figure 13C:
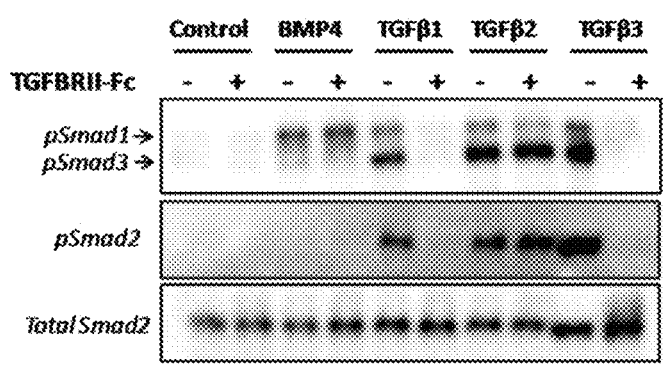
Figure 13D:
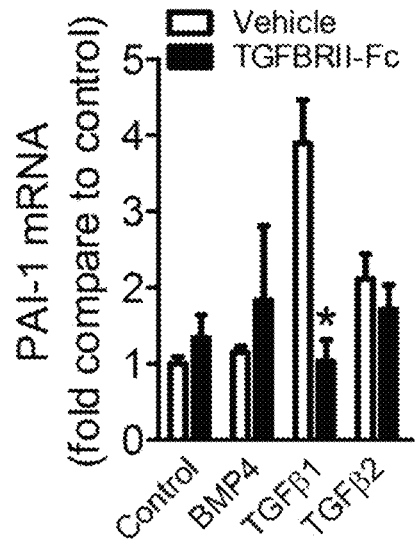
Figure 14:
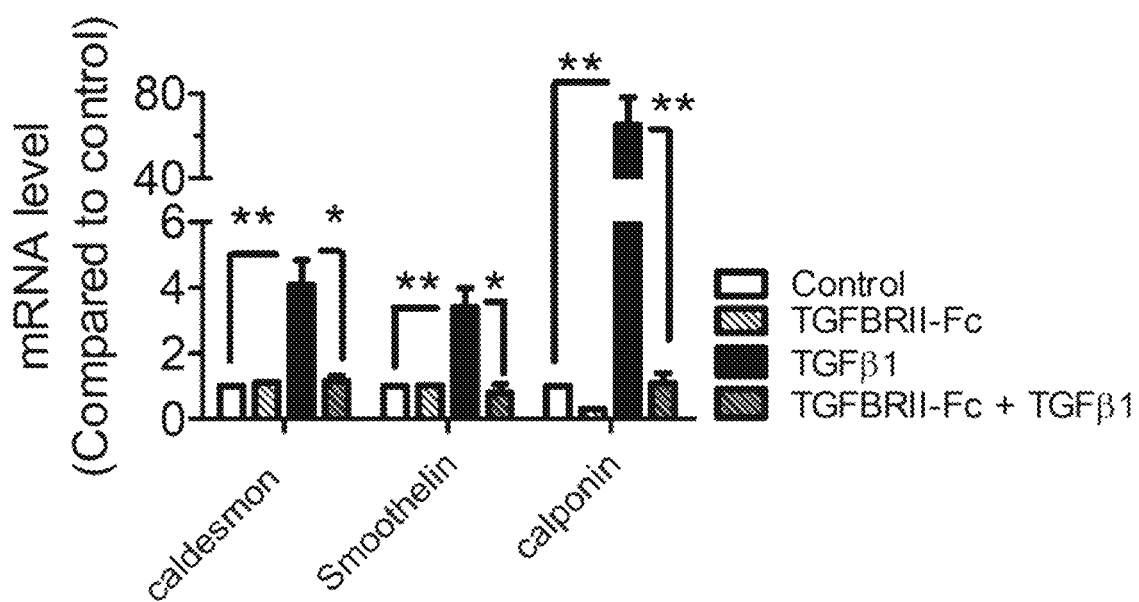
FIG. 14 demonstrates that TGFBRII-Fc prevented TGFβ-induced SMC plasticity switch. HPASMC were deprived of serum overnight and then exposed to TGFβ1 (1 ng/ml), with or without TGFBRII-Fc (2000 ng/ml) for 24 hours. mRNA level of SMC contractile markers was examined. Data are mean±SEM, * $p<0.05$,  $p<0.01$, * $P<0.001$ as indicated.

TGFBRII-Fc is a recombinant fusion protein consists of ligand bind domain of TGFβ type II receptor. TGFBRII-Fc selectively inhibited the activity of TGFβ1 and 3 in inducing TGF-β transcriptional activity measured by a CAGA-Luc reporter cell line, while failing to suppress, or modestly enhancing the activity of TGF-β2 (FIG. 13A). In contrast, treatment with TGFBRII-Fc did not inhibit BMP-mediated transcriptional activity in a BRE-Luc reporter line, and in fact enhanced the activity of several ligands in this assay (FIG. 13B). These results were consistent with selective activity of this ligand trap against a subset of TGF-β ligands, and suggested feedback mechanisms whereby suppression of TGF-β signaling could result in enhanced BMP and TGF-β2 signaling. Consistently, TGFBRII-Fc prevented TGFβ1- and TGFβ3-induced Smad 2/3 phosphorylation (FIG. 13C), without affecting TGFβ2-induced signaling, in cultured human pulmonary artery smooth muscle cell (HPASMC). Consistently, TGFBRII-Fc prevented TGFβ1-induced signaling in HPASMC. When HPASMC were stimulated with TGF-β1, the expression of smooth muscle contractile phenotype genes such as caldesmon, smoothelin, and particularly calponin as measured by qRT-PCR was enhanced, all of which were potently inhibited by the co-treatment of cells with TGFBRII-Fc (FIG. 14). Taken together, TGFBRII-Fc appeared to be a potent antagonist of TGF-β1 and β3 and can abrogate their effects on vascular smooth muscle cells in vitro.

In the rat MCT-induced model of PAH, we confirmed that the development of PAH was associated with diminished BMPR2/BMP-mediated signaling and gene transcription in whole lungs, along with a marked increase in TGFβ-mediated signaling and transcription, consistent with previous reports[30]. Rats subjected to MCT showed elevated right ventricular systolic pressure (RVSP) and elevated Fulton's ratio consistent with right heart hypertrophy (RVH) evolving in a time-dependent fashion within 3 weeks after MCT treatment. MCT exposure led to progressive increase in Pai1 and Tgfb1 mRNA levels as previously reported. Meanwhile, the expression of Bmpr2 and Id1 mRNA was reduced in rats treated with MCT Enhanced TGFβ signaling activity, assessed by Tgfb1 and Pai1 expression, was directly correlated with disease severity, as measured by RVSP and Fulton's ratio, as was the impairment of BMP signaling activity, assessed by Bmpr2 and Id1 expression.

We tested the hypothesis that TGFBRII-Fc could act as a selective ligand trap to inhibit TGFβ1/3 signaling activity in vivo and modulate disease progression in experimental PAH. Treatment with low dose of TGFBRII-Fc (5 mg/kg, twice per week) showed a non-significant trend towards reduced RVSP, RVH, and muscularization of small pulmonary vessels, but significantly decreased medial wall thickness index following MCT-induced pulmonary arterial hypertension. A high-dose regimen of TGFBRII-Fc (15 mg/kg, twice per week) significantly reduced RVSP (46.72±4.68 vs. 32.99±2.08 mmHg) as well as RVH (0.52±0.04 vs. 0.41±0.02). TGFBRII-Fc treatment under this regimen effectively prevented vascular remodeling in MCT rats (FIGS. 4A-4M). MCT-treated rats receiving TGFBRII-Fc exhibited reduced mRNA levels of Pai1, and unexpectedly also reduced levels of Tgfb1 (FIG. 4A-4M) in total lungs extracts. The reduced mRNA levels of Bmpr2 and Id1 in MCT-treated rats were unaffected by TGFBRII-Fc treatment. We also found that TGFBRII-Fc treatment reduced Il6, Il1b and Icam (FIG. 4A-4M) mRNA levels in lungs of MCT-rats. Consistent with enhanced TGF-β signaling activity, MCT treatment of rats was associated with increased expression of phosphorylated SMAD2, detected by immunohistochemistry of lung sections of mice primarily in the nuclei of vascular cells. Treatment with TGFBRII-Fc attenuated this increased level of phosphorylated SMAD2 (data not shown).

Figure 18:
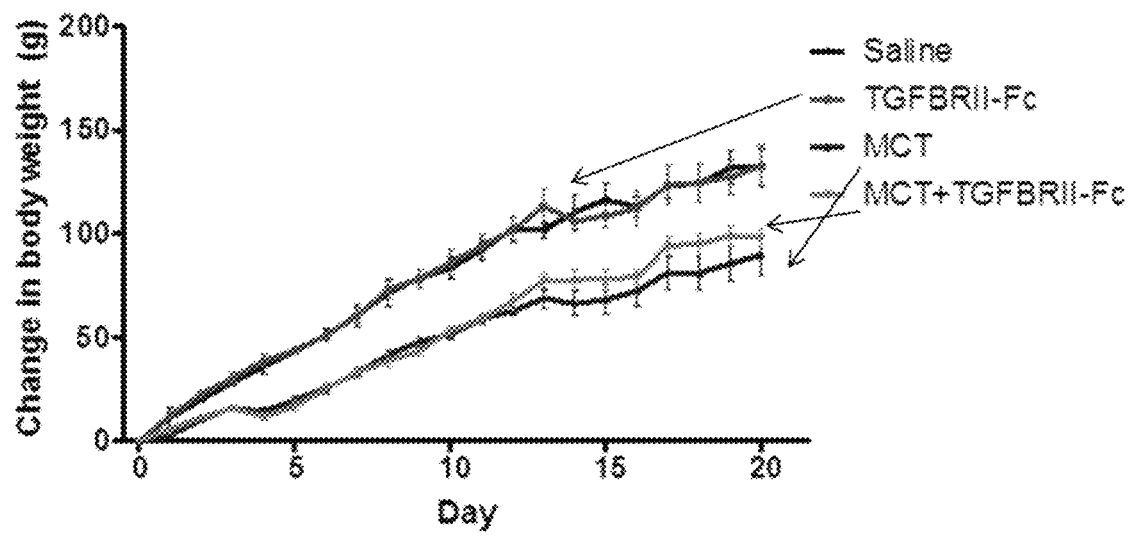
FIG. 18 demonstrates that body weight of control and MCT rats receiving vehicle or TGFBRII-Fc treatment. Adult male SD rats treated with MCT (40 mg/kg SC×1) were administered TGFBRII-Fc (15 mg/kg IP twice weekly) or vehicle for 3 weeks. TGFBRII-Fc treatment did not impact body weight in rats.
Figure 19:
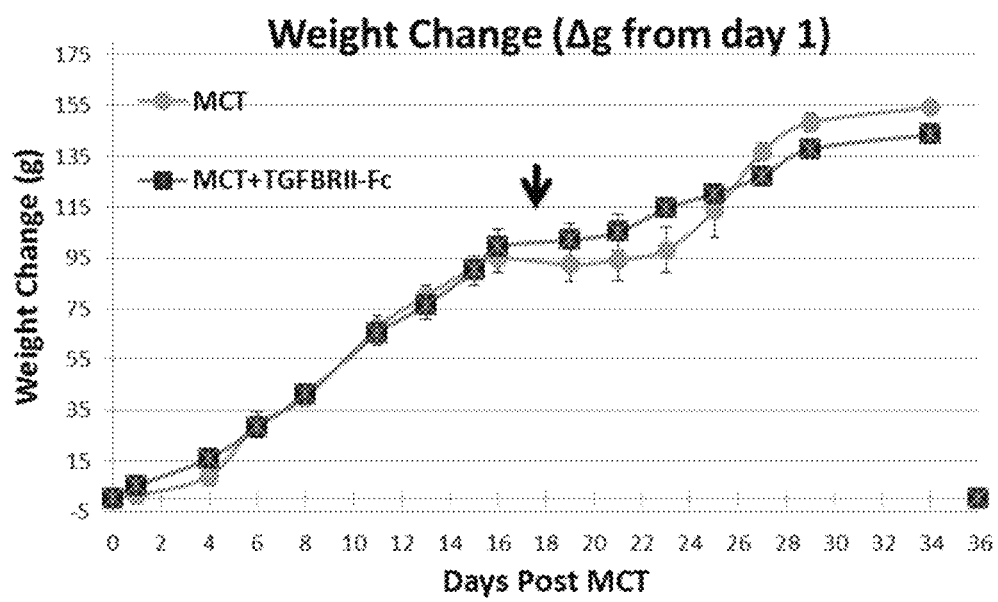
FIG. 19 demonstrates that body weight of MCT rats with delayed TGFBRII-Fc treatment. Adult male SD rats treated with MCT (40 mg/kg SC×1) and observed for 18 days before receiving the TGFBRII-Fc treatment (15 mg/kg IP three times weekly). Hemodynamics and remodeling were examined on day 35. TGFBRII-Fc treatment did not impact body weight in rats.

Echocardiographic assessment provided an alternative measurement of RVH, showing that treatment with TGFBRII-Fc attenuated the increase in RV free-wall thickness observed in MCT rats at day 14 (0.77±0.15 vs. 0.59±0.11 mm, p<0.05). We also observed a reduced pulmonary acceleration time (PAT) in MCT rats (19.83±2.60 vs. 32.64±2.16 ms, p<0.05), which was unaffected by TGFBRII-Fc treatment. Echocardiographic M-mode and 2D assessment did not reveal evidence of valvular dysfunction or degeneration as a result of TGFBRII-Fc administration in normal or MCT-treated rats. Importantly, treatment with TGFBRII-Fc was also not associated with morphological changes in mitral valve structure, with no evidence of sclerotic or degenerative remodeling (FIGS. 17A-17B). Treatment with TGFBRII-Fc in normal or MCT-treated rats did not modify the normal gains in weight that were seen in vehicle treatment (FIGS. 18 and 19).

We tested the ability of TGFBRII-Fc to impact established PAH in the MCT model. Treatment of TGFBRII-Fc (15 mg/kg, three times per week) was started at 18 days after MCT exposure, and hemodynamics and RVH were measured at 35 days. When administered in this delayed fashion, TGFBRII-Fc improved survival, reduced RVSP (43.18±3.46 vs. 33.29±0.77 mmHg, p<0.01) and vascular remodeling (p<0.05) in MCT-treated rats with established PAH. However, RVH is not affected by the delayed treatment of TGFBRII-Fc (0.44±0.03 vs. 0.42±0.02). Of note, the improvement in vascular remodeling in rescue cohort treated in this fashion was more pronounced than that observed in prophylaxis cohort. This observation was made with a higher dose of TGFBRII-Fc than that used in the prophylaxis studies, suggesting that the therapeutic potential of this ligand trap in vascular remodeling is dose-sensitive and can be maximized by titrating its dosage to optimal effect. We also found that TGFBRII-Fc treatment reduced the mRNA expression of Tgfb1 (FIG. 15A), Pai1 (FIG. 15B), 116 (FIG. 15C), Mb (FIG. 15D), and Icam (FIG. 15E) in lungs of MCT-rats. When MCT-treated rats with established PAH were treated with TGFBRII-Fc, a decrease in phosphorylated SMAD2 primarily observed in the nuclei of vascular cells was observed (data not shown).

Figure 20A:
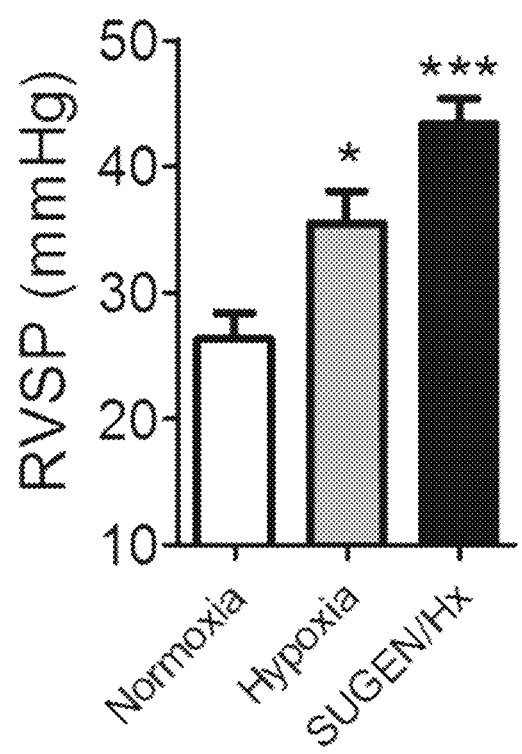
FIGS. 20A-20B depict experiments in which adult male C57 BL6/J mice were randomized and subjected to normoxia, hypoxia, or SUGEN+hypoxia for 3 weeks. RVSP (a) and right ventricular hypertrophy (b) were measured and compared to normoxia mice (n=5-8, *p<0.05, p<0.01, *p<0.001 compared to control).
Figure 20B:
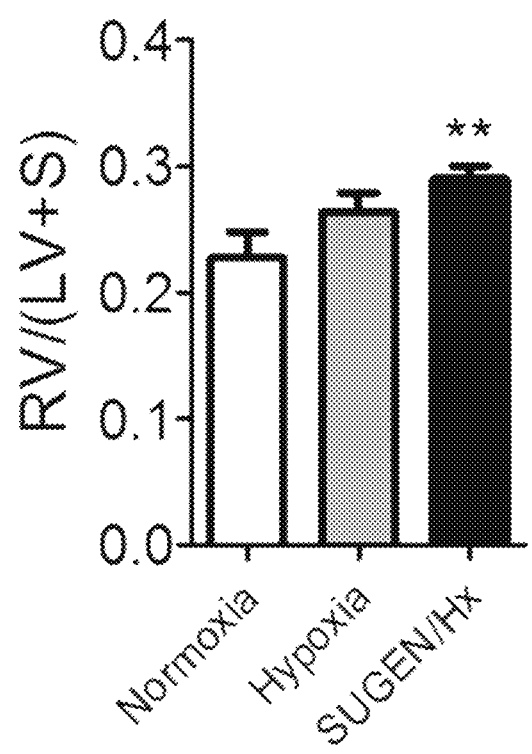

We next examined the efficacy of TGFBRII-Fc in the SUGEN/hypoxia model. Mice were treated with VEGFR inhibitor SU5416 and exposed to chronic hypoxia for 3 weeks to provide a mechanistically distinct and complementary model of PAH. Combined treatment of SUGEN and hypoxia triggered a much more robust and consistent phenotypes in mice exposed to hypoxia alone (FIGS. 20A-20B). Prophylactic treatment with TGFBRII-Fc significantly reduced RVSP (43.38±5.66 vs. 35.42±5.85 mmHg, $p<0.05$) and RVH (0.29±0.01 vs. 0.24±0.02, $p<0.05$) in SUGEN/hypoxia-treated mice. TGFBRII-Fc treatment attenuated vascular remodeling in lungs of SUGEN/hypoxia-treated mice (data not shown). We also found that TGFBRII-Fc treatment showed a trend towards reversing the up-regulation of Tgfb1 (FIG. 16A) and significantly reduced Pai1 mRNA level in the lungs of SUGEN/hypoxia mice (FIG. 16B).

DISCUSSION

Based on the known importance of TGFβ signaling in pulmonary vascular function and disease, and the structural and functional diversity of these ligands, we sought to determine if selective inhibition of TGFβ signaling could attenuate experimental pulmonary hypertension and pulmonary vascular remodeling. We characterized recombinant TGFBRII-Fc fusion protein as a potent inhibitor of TGFβ1 and TGFβ3 ligand signaling that does not affect the signaling of TGFβ2, an important regulator of endothelial-to-mesenchymal transition, extracellular matrix remodeling, and cardiac valve formation[25,27]. Consistent with this activity, TGFBRII-Fc blocked canonical SMAD2/3 signaling via TGFβ1 and TGFβ3, and prevented TGFβ1-mediated switching of pulmonary artery smooth muscle cells from a synthetic to a contractile phenotype in vitro[31,32]. We hypothesized that TGFβ1/3 are primarily responsible for mediating pulmonary vascular remodeling seen in PAH, and found in two distinct models of PAH that TGFBRII-Fc treatment corrected excessive TGFβ signaling activity and attenuated pulmonary vascular remodeling, pulmonary hypertension, and right ventricular hypertrophy. Importantly, TGFBRII-Fc not only prevented the progression of established PAH and RVH in rats previously treated with monocrotaline, but improved their survival as well. These present data are the first demonstration that selectively inhibiting a subset of TGFβ ligands attenuates PAH, and does so in mechanistically distinct models of PAH, using a strategy that is likely more tolerable than non-selective approaches.

The TGFβ family of signaling molecules represent a structurally diverse set of more than 35 multifunctional cytokines that regulate the differentiation, proliferation, migration and survival of many different cell types, including BMPs, Activins, Inhibins, Growth and Differentiation Factors (GDFs), Lefty, Nodal, and Anti-Mullerian Hormone in addition to TGFβ1-3. TGFβ type ligands orchestrate numerous processes during embryogenesis, and play critical roles in the pathophysiologic remodeling seen in vascular and fibrotic diseases, roles that have generated tremendous interest in their blockade for therapeutic applications[20,33-37]. Non-selective blockade of TGFβ signaling has been shown to be helpful in monocrotaline-induced PAH in rats. Small molecule inhibitors IN-1333, SD-208, and SB-525334 attenuate monocrotaline-induced PAH purportedly by inhibiting TGFβ signaling via the activity of its type I receptor ALK5[13,17,30]. However, all of these molecules demonstrate potent activity for closely related type I receptors ALK4 and ALK7[38-40] and would affect the activity of not only TGFβ1-3 but potentially 20 other ligands including Activins, GDFs, and Nodal whose functions may or may not be concordant with TGFβ in the vasculature. Moreover, these potent TGFβ inhibitors appear to have a class-wide effect of causing hemorrhagic valve necrosis in animals[18], potentially due to their lack of selectivity, and presenting a challenge for their use in man. The pan-TGFβ1-3 neutralizing antibody 1D11 has also been effective in mitigating monocrotaline-induced PAH, [20,39].

The administration of TGFBRII-Fc did not impact the function or structure of cardiac valves, based on echocardiographic and histological analysis of treated vs. untreated animals. Despite possible limitations in the tolerability of non-selective strategies. The concordance of these distinct strategies to improve pulmonary vascular remodeling is strong evidence for the role of this signaling axis in PAH, however, several limitations for advancing this concept clinically have existed.

A significant limitation of these previous studies relied on one preclinical model of monocrotaline-induced PAH. The lungs of MCT-induced PAH in the rat have a molecular signature of exaggerated TGF-β signaling and pro-fibrotic transcriptional activity, suppressed expression of BMPR2 and downstream BMP signaling activity[30], and evidence of diffuse inflammation and lung injury[41], as we found in the current study, which might make them particularly amenable to TGFβ ligand blockade. While the molecular profile of MCT-PAH resembles that of some types of human PAH disease, it would be helpful to know whether or not the effects of TGFβ antagonism are generalizable to other models. When we examined the impact of TGFBRII-Fc in the mechanistically distinct SUGEN-hypoxia induced model of PAH in mice, as has been recently validated by other investigators[42,43], we found an increase in the expression of TGFβ transcriptional targets such as Pai1, but to a lesser extent than that seen in MCT-treated rats. Nonetheless, treatment of these animals with TGFBRII-Fc was also seen to improve PA pressures and RV hypertrophy.

Clinical deployment of small molecule inhibitors against ALK5 has been limited by toxicities. TGFβ2 signaling is essential for cardiac valve morphogenesis, consistent with its central role in regulating endothelial- and epithelial-to-mesenchymal transition in a variety of tissues[21-29]. Consistent with the concept that the native TGF-β type II receptor does not transduce TGFβ2 signals in the absence of the type III co-receptor betaglycan[44-46], soluble TGFBRII-Fc did not affect TGFβ2-induced signaling in vitro, and when administered to mice and rats chronically at doses sufficient to mitigate PAH, TGFBRII-Fc did not cause any observable changes in cardiac valve structure or function, or cause any increase in mortality previously observed with non-selective TGFβ antagonism. On the contrary, treatment with TGFBRII-Fc was well tolerated and improved mortality as an endpoint in rescue studies.

PAH is caused by pulmonary vascular remodeling that involves multiple cell types. Consistent with observations from Thomas and colleagues, we observed increased phospho-Smad2 staining that co-localized to mononucleated cells in lungs of MCT rats[17]. It is also shown that CD68-positive cells infiltrated into the affected lungs of MCT-rats contributed to the over-production of TGF-β1[30]. Without wishing to be limited by theory, taken together, these data suggest infiltrating cells could be the primary cell type responsible for excessive TGF-β signaling activity in experimental PAH. Our data showed that TGFβ1 modulated SMC phenotypes in vitro, a process that is reversed by TGFBRII-Fc.

Provided herein is data showing a soluble TGF-β type II receptor acts as a selective ligand trap against TGF-β1/3, attenuating vascular remodeling and improving PAH concurrent with vascular injury and in established disease. Unlike previous approaches, administration of this selective ligand trap did not cause cardiac valvular or other toxicities. Thus, selective ligand traps of specific TGF-β ligands can be effective and tolerable approaches to treating human PAH.

REFERENCES

1. Megalou A J, Glava C, Oikonomidis D L, Vilaeti A, Agelaki M G, Baltogiannis G G, Papalois A, Vlahos A P, Kolettis T M. Transforming growth factor-beta inhibition attenuates pulmonary arterial hypertension in rats. *Int J Chn Exp Med.* 2010; 3:332-340
2. Strelau J, Schober A, Sullivan A, Schilling L, Unsicker K. Growth/differentiation factor-15 (gdf-15), a novel member of the tgf-beta superfamily, promotes survival of lesioned mesencephalic dopaminergic neurons in vitro and in vivo and is induced in neurons following cortical lesioning. *J Neural Transm Suppl.* 2003:197-203
3. Deng Z, Morse J H, Slager S L, Cuervo N, Moore K J, Venetos G, Kalachikov S, Cayanis E, Fischer S G, Barst R J, Hodge S E, Knowles J A. Familial primary pulmonary hypertension (gene pphl) is caused by mutations in the bone morphogenetic protein receptor-ii gene. *Am J Hum Genet.* 2000; 67:737-744
4. Lane K B, Machado R D, Pauciulo M W, Thomson J R, Phillips J A, 3rd, Loyd J E, Nichols W C, Trembath R C. Heterozygous germline mutations in bmpr2, encoding a tgf-beta receptor, cause familial primary pulmonary hypertension. The international pph consortium. *Nat Genet.* 2000; 26:81-84
5. Waite K A, Eng C. From developmental disorder to heritable cancer: It's all in the bmp/tgf-beta family. *Nat Rev Genet.* 2003; 4:763-773
6. Yu P B, Deng D Y, Beppu H, Hong C C, Lai C, Hoyng S A, Kawai N, Bloch K D. Bone morphogenetic protein (bmp) type ii receptor is required for bmp-mediated growth arrest and differentiation in pulmonary artery smooth muscle cells. *J Biol Chem.* 2008; 283:3877-3888
7. Rudarakanchana N, Flanagan J A, Chen H, Upton P D, Machado R, Patel D, Trembath R C, Morrell N W. Functional analysis of bone morphogenetic protein type ii receptor mutations underlying primary pulmonary hypertension. *Hum Mol Genet.* 2002; 11:1517-1525
8. Yu P B, Beppu H, Kawai N, Li E, Bloch K D. Bone morphogenetic protein (bmp) type ii receptor deletion reveals bmp ligand-specific gain of signaling in pulmonary artery smooth muscle cells. *J Biol Chem.* 2005; 280:24443-24450
9. Moon J S, Oh S H, Jeong Y W, Kang J H, Park J C, Son H J, Bae S, Park B I, Kim M S, Koh J T, Kim S H, Ko H M. Relaxin augments bmp 2-induced osteoblast differentiation and bone formation. *J Bone Miner Res.* 2014
10. Eggers K M, Kempf T, Lagerqvist B, Lindahl B, Olofsson S, Jantzen F, Peter T, Allhoff T, Siegbahn A, Venge P, Wollert K C, Wallentin L. Growth-differentiation factor-15 for long-term risk prediction in patients stabilized after an episode of non-st-segment-elevation acute coronary syndrome. *Circ Cardiovasc Genet.* 2010; 3:88-96
11. Tuder R M, Davis L A, Graham B B. Targeting energetic metabolism: A new frontier in the pathogenesis and treatment of pulmonary hypertension. *Am J Respir Crit Care Med.* 2012; 185:260-266
12. Botney M D, Bahadori L, Gold L I. Vascular remodeling in primary pulmonary hypertension. Potential role for transforming growth factor-beta. *Am J Pathol.* 1994; 144:286-295
13. Zaiman A L, Podowski M, Medicherla S, Gordy K, Xu F, Zhen L, Shimoda L A, Neptune E, Higgins L, Murphy A, Chakravarty S, Protter A, Sehgal P B, Champion H C, Tuder R M. Role of the tgf-beta/alk5 signaling pathway in monocrotaline-induced pulmonary hypertension. *Am J Respir Crit Care Med.* 2008; 177:896-905
14. Chen Y F, Feng J A, Li P, Xing D, Zhang Y, Serra R, Ambalavanan N, Majid-Hassan E, Oparil S. Dominant negative mutation of the tgf-beta receptor blocks hypoxia-induced pulmonary vascular remodeling. *J Appl Physiol.* 2006; 100:564-571
15. Sheares K K, Jeffery T K, Long L, Yang X, Morrell N W. Differential effects of tgf-beta1 and bmp-4 on the hypoxic induction of cyclooxygenase-2 in human pulmonary artery smooth muscle cells. *Am J Physiol Lung Cell Mol Physiol.* 2004; 287:L919-927
16. Graham B B, Chabon J, Gebreab L, Poole J, Debella E, Davis L, Tanaka T, Sanders L, Dropcho N, Bandeira A, Vandivier R W, Champion H C, Butrous G, Wang X J, Wynn T A, Tuder R M. Transforming growth factor-beta signaling promotes pulmonary hypertension caused by *Schistosoma mansoni. Circulation.* 2013; 128:1354-1364
17. Thomas M, Docx C, Holmes A M, Beach S, Duggan N, England K, Leblanc C, Lebret C, Schindler F, Raza F, Walker C, Crosby A, Davies R J, Morrell N W, Budd D C. Activin-like kinase 5 (alk5) mediates abnormal proliferation of vascular smooth muscle cells from patients with familial pulmonary arterial hypertension and is involved in the progression of experimental pulmonary arterial hypertension induced by monocrotaline. *Am J Pathol.* 2009; 174:380-389
18. Anderton M J, Mellor H R, Bell A, Sadler C, Pass M, Powell S, Steele S J, Roberts R R, Heier A. Induction of heart valve lesions by small-molecule alk5 inhibitors. *Toxicol Pathol.* 2011; 39:916-924
19. Megalou A J, Glava C, Vilaeti A D, Oikonomidis D L, Baltogiannis G G, Papalois A, Vlahos A P, Kolettis T M. Transforming growth factor-beta inhibition and endothelin receptor blockade in rats with monocrotaline-induced pulmonary hypertension. *Pulm Circ.* 2012; 2:461-469
20. Grafe I, Yang T, Alexander S, Homan E P, Lietman C, Jiang M M, Bertin T, Munivez E, Chen Y, Dawson B, Ishikawa Y, Weis M A, Sampath T K, Ambrose C, Eyre D, Bachinger H P, Lee B. Excessive transforming growth factor-beta signaling is a common mechanism in osteogenesis imperfecta. *Nature medicine.* 2014; 20:670-675
21. Shin J A, Hong O K, Lee H J, Jeon S Y, Kim J W, Lee S H, Cho J H, Lee J M, Choi Y H, Chang S A, Son H Y, Kim J H, Yoon K H. Transforming growth factor-beta induces epithelial to mesenchymal transition and suppresses the proliferation and transdifferentiation of cultured human pancreatic duct cells. *J Cell Biochem.* 2011; 112:179-188
22. Azhar M, Runyan R B, Gard C, Sanford L P, Miller M L, Andringa A, Pawlowski S, Rajan S, Doetschman T. Ligand-specific function of transforming growth factor beta in epithelial-mesenchymal transition in heart development. *Developmental dynamics: an official publication of the American Association of Anatomists.* 2009; 238: 431-442
23. Camenisch T D, Molin D G, Person A, Runyan R B, Gittenberger-de Groot A C, McDonald J A, Klewer S E. Temporal and distinct tgfbeta ligand requirements during mouse and avian endocardial cushion morphogenesis. *Dev Biol.* 2002; 248:170-181
24. Saito R A, Watabe T, Horiguchi K, Kohyama T, Saitoh M, Nagase T, Miyazono K. Thyroid transcription factor-1 inhibits transforming growth factor-beta-mediated epithelial-to-mesenchymal transition in lung adenocarcinoma cells. *Cancer Res.* 2009; 69:2783-2791
25. Kokudo T, Suzuki Y, Yoshimatsu Y, Yamazaki T, Watabe T, Miyazono K. Snail is required for tgfbeta-induced endothelial-mesenchymal transition of embryonic stem cell-derived endothelial cells. *Journal of cell science.* 2008; 121:3317-3324
26. Townsend T A, Robinson J Y, Deig C R, Hill C R, Misfeldt A, Blobe G C, Barnett J V. Bmp-2 and tgfbeta2 shared pathways regulate endocardial cell transformation. *Cells Tissues Organs.* 2011; 194:1-12
27. Azhar M, Brown K, Gard C, Chen H, Rajan S, Elliott D A, Stevens M V, Camenisch T D, Conway S J, Doetschman T. Transforming growth factor beta2 is required for valve remodeling during heart development. *Developmental dynamics: an official publication of the American Association of Anatomists.* 2011; 240:2127-2141
28. Townsend T A, Robinson J Y, How T, DeLaughter D M, Blobe G C, Barnett J V. Endocardial cell epithelial-mesenchymal transformation requires type iii tgfbeta receptor interaction with gipc. *Cell Signal.* 2012; 24:247-256
29. Medici D, Shore E M, Lounev V Y, Kaplan F S, Kalluri R, Olsen B R. Conversion of vascular endothelial cells into multipotent stem-like cells. *Nature medicine.* 2010; 16:1400-1406
30. Long L, Crosby A, Yang X, Southwood M, Upton P D, Kim D K, Morrell N W. Altered bone morphogenetic protein and transforming growth factor-beta signaling in rat models of pulmonary hypertension: Potential for activin receptor-like kinase-5 inhibition in prevention and progression of disease. *Circulation.* 2009; 119:566-576
31. Davis B N, Hilyard A C, Lagna G, Hata A. Smad proteins control drosha-mediated microrna maturation. *Nature.* 2008; 454:56-61
32. King K E, Iyemere V P, Weissberg P L, Shanahan C M. Kruppel-like factor 4 (klf4/gklf) is a target of bone morphogenetic proteins and transforming growth factor beta 1 in the regulation of vascular smooth muscle cell phenotype. *The Journal of biological chemistry.* 2003; 278:11661-11669
33. Cohn R D, van Erp C, Habashi J P, Soleimani A A, Klein E C, Lisi M T, Gamradt M, ap Rhys C M, Holm T M, Loeys B L, Ramirez F, Judge D P, Ward C W, Dietz H C. Angiotensin ii type 1 receptor blockade attenuates tgf-beta-induced failure of muscle regeneration in multiple myopathic states. *Nature medicine.* 2007; 13:204-210
34. Ng C M, Cheng A, Myers L A, Martinez-Murillo F, Jie C, Bedja D, Gabrielson K L, Hausladen J M, Mecham R P, Judge D P, Dietz H C. Tgf-beta-dependent pathogenesis of mitral valve prolapse in a mouse model of marfan syndrome. *The Journal of clinical investigation.* 2004; 114:1586-1592
35. Gallo E M, Loch D C, Habashi J P, Calderon J F, Chen Y, Bedja D, van Erp C, Gerber E E, Parker S J, Sauls K, Judge D P, Cooke S K, Lindsay M E, Rouf R, Myers L, ap Rhys C M, Kent K C, Norris R A, Huso D L, Dietz H C. Angiotensin ii-dependent tgf-beta signaling contributes to loeys-dietz syndrome vascular pathogenesis. *The Journal of clinical investigation.* 2014; 124:448-460
36. Wu C F, Chiang W C, Lai C F, Chang F C, Chen Y T, Chou Y H, Wu T H, Linn G R, Ling H, Wu K D, Tsai T J, Chen Y M, Duffield J S, Lin S L. Transforming growth factor beta-1 stimulates profibrotic epithelial signaling to activate pericyte-myofibroblast transition in obstructive kidney fibrosis. *Am J Pathol.* 2013; 182:118-131
37. Ling H, Roux E, Hempel D, Tao J, Smith M, Lonning S, Zuk A, Arbeeny C, Ledbetter S. Transforming growth factor beta neutralization ameliorates pre-existing hepatic fibrosis and reduces cholangiocarcinoma in thioacetamide-treated rats. *PLoS One.* 2013; 8:e54499
38. Grygielko E T, Martin W M, Tweed C, Thornton P, Harling J, Brooks D P, Laping N J. Inhibition of gene markers of fibrosis with a novel inhibitor of transforming growth factor-beta type i receptor kinase in puromycin-induced nephritis. *The Journal of pharmacology and experimental therapeutics.* 2005; 313:943-951
39. Kim D K, Sheen Y Y, Jin C H, Park C Y, Sreenu D, Rao K S, Krishnaiah M, Subrahmanyam V B. 2-pyridyl substituted imidazoles as therapeutic alk5 and/or alk4 inhibitors. *World Intellectual Property Organization.* 2011; US20110319406 A1
40. Loots G G, Keller H, Leupin O, Murugesh D, Collette N M, Genetos D C. Tgf-beta regulates sclerostin expression via the ecr5 enhancer. *Bone.* 2012; 50:663-669
41. Gomez-Arroyo J G, Farkas L, Alhussaini A A, Farkas D, Kraskauskas D, Voelkel N F, Bogaard H J. The monocrotaline model of pulmonary hypertension in perspective. *Am J Physiol Lung Cell Mol Physiol.* 2012; 302: L363-369
42. Ciuclan L, Bonneau O, Hussey M, Duggan N, Holmes A M, Good R, Stringer R, Jones P, Morrell N W, Jarai G, Walker C, Westwick J, Thomas M. A novel murine model of severe pulmonary arterial hypertension. *American journal of respiratory and critical care medicine.* 2011; 184:1171-1182
43. Bertero T, Lu Y, Annis S, Hale A, Bhat B, Saggar R, Wallace W D, Ross D J, Vargas S O, Graham B B, Kumar R, Black S M, Fratz S, Fineman J R, West J D, Haley K J, Waxman A B, Chau B N, Cottrill K A, Chan S Y. Systems-level regulation of microrna networks by mir-130/301 promotes pulmonary hypertension. *The Journal of clinical investigation.* 2014; 124:3514-3528
44. Esparza-Lopez J, Montiel J L, Vilchis-Landeros M M, Okadome T, Miyazono K, Lopez-Casillas F. Ligand binding and functional properties of betaglycan, a co-receptor of the transforming growth factor-beta superfamily. Specialized binding regions for transforming growth factor-beta and inhibin a. *The Journal of biological chemistry.* 2001; 276:14588-14596
45. Brown C B, Boyer A S, Runyan R B, Barnett J V. Requirement of type iii tgf-beta receptor for endocardial cell transformation in the heart. *Science.* 1999; 283:2080-2082

46. Blobe G C, Schiemann W P, Pepin M C, Beauchemin M, Moustakas A, Lodish H F, O'Connor-McCourt M D. Functional roles for the cytoplasmic domain of the type iii transforming growth factor beta receptor in regulating transforming growth factor beta signaling *The Journal of biological chemistry*. 2001; 276:24627-24637

```
human GDF-15 NCBI Ref Seq: NP_004855
                                                                SEQ ID NO: 1
  1   mpgqelrtvn gsqmllvllv lswlphggal slaeasrasf pgpselhsed srfrelrkry
 61   edlltrlran qswedsntdl vpapavrilt pevrlgsggh lhlrisraal peglpeasrl
121   hralfrlspt asrswdvtrp lrrqlslarp qapalhlrls pppsqsdqll aesssarpql
181   elhlrpqaar grrrararng dhcplgpgrc crlhtvrasl edlgwadwvl sprevqvtmc
241   igacpsqfra anmhaqikts lhrlkpdtvp apccvpasyn pmvliqktdt gyslqtyddl
301   lakdchci human TGFβ1 NCBI Ref Seq: NP_000651
                                                                SEQ ID NO: 2
  1   mppsglrllp lllpllwllv ltpgrpaagl stcktidmel vkrkrieair gqilsklrla
 61   sppsqgevpp gplpeavlal ynstrdrvag esaepepepe adyyakevtr vlmvethnei
121   ydkfkqsths iymffntsel reavpepvll sraelrllrl klkveqhvel yqkysnnswr
181   ylsnrllaps dspewlsfdv tgvvrqwlsr ggeiegfrls ahcscdsrdn tlqvdingft
241   tgrrgdlati hgmnrpflll matpleraqh lqssrhrral dtnycfsste knccvrqlyi
301   dfrkdlgwkw ihepkgyhan fclgpcpyiw sldtgyskvl alynqhnpga saapccvpqa
361   leplpivyyv grkpkveqls nmivrsckcs human TGFβ3 NCBI Ref Seq: NP_003230
                                                                SEQ ID NO: 3
  1   mkmhlqralv vlallnfatv slslstcttl dfghikkkrv eairgqilsk lrltspppept
 61   vmthvpyqvl alynstrell eemhgereeg ctqentesey yakeihkfdm iqglaehnel
121   avcpkgitsk vfrfnvssve knrtnlfrae frvlrvpnps skrneqriel fqilrpdehi
181   akqryiggkn lptrgtaewl sfdvtdtvre wllrresnlg leisihcpch tfqpngdile
241   nihevmeikf kgvdneddhg rgdlgrlkkq kdhhnphlil mmipphrldn pgqggqrkkr
301   aldtnycfrn leenccvrpl yidfrqdlgw kwvhepkgyy anfcsgpcpy lrsadtthst
361   vlglyntlnp easaspccvp qdlepltily yvgrtpkveq lsnmvvksck cs human TGFBR2 NCBI Ref Seq: NP_001020018
                                                                SEQ ID NO: 4
  1   mgrgllrglw plhivlwtri astipphvqk sdvemeaqkd eiicpscnrt ahplrhinnd
 61   mivtdnngav kfpqlckfcd vrfstcdnqk scmsncsits icekpqevcv avwrkndeni
121   tletvchdpk lpyhdfiled aaspkcimke kkkpgetffm cscssdecnd niifseeynt
181   snpdlllvif qvtgisllpp lgvaisviii fycyrvnrqq klsstwetgk trklmefseh
241   caiileddrs disstcanni nhntellpie ldtlvgkgrf aevykaklkq ntseqfetva
301   vkifpyeeya swktekdifs dinlkhenil qfltaeerkt elgkqywlit afhakgnlqe
361   yltrhviswe dlrklgssla rgiahlhsdh tpcgrpkmpi vhrdlkssni lvkndltccl
421   cdfglslrld ptlsvddlan sgqvgtarym apevlesrmn lenvesfkqt dvysmalvlw
481   emtsrcnavg evkdyeppfg skvrehpcve smkdnvlrdr grpeipsfwl nhqgiqmvce
541   tltecwdhdp earltaqcva erfselehld rlsgrscsee kipedgslnt tk
```

What is claimed herein is:

1. A method of treating pulmonary arterial hypertension (PAH) in a subject in need of treatment thereof, the method comprising administering a neutralizing antibody against Growth Differentiation Factor 15 (GDF-15) to the subject.

2. The method of claim 1, wherein the subject has scleroderma or connective tissue disease associated with PAH (APAH-CTD).

3. The method of claim 1, wherein the subject is determined to have an increased level of GDF-15 relative to a control.

* * * * *